United States Patent
DeBonte et al.

(10) Patent No.: US 7,135,614 B1
(45) Date of Patent: Nov. 14, 2006

(54) BRASSICA OR HELIANTHUS PLANTS HAVING MUTANT DELTA-12 OR DELTA-15 SEQUENCES

(75) Inventors: Lorin R. DeBonte, Ft. Collins, CO (US); Zhegong Fan, Colorado Springs, CO (US); Guo-Hua Miao, Johnston, IA (US)

(73) Assignee: Cargill, Incorporated, Minneapolis, MN (US)

( * ) Notice: Subject to any disclaimer, the term of this patent is extended or adjusted under 35 U.S.C. 154(b) by 0 days.

(21) Appl. No.: 08/572,027

(22) Filed: Dec. 14, 1995

Related U.S. Application Data

(63) Continuation-in-part of application No. 08/416,497, filed on Apr. 4, 1995, now Pat. No. 5,668,299, which is a continuation of application No. 08/170,886, filed on Dec. 21, 1993, now abandoned, which is a continuation-in-part of application No. 07/739,965, filed on Aug. 5, 1991, now abandoned, which is a continuation-in-part of application No. 07/575,542, filed on Aug. 30, 1990, now abandoned.

(51) Int. Cl.
*A01H 5/00* (2006.01)
*A01H 1/06* (2006.01)
*C07H 21/02* (2006.01)

(52) U.S. Cl. .................. 800/264; 800/270; 536/23.1

(58) Field of Classification Search ............. 800/205, 800/264, 270, 306, 298, 320.1, 261, 281; 536/27.1, 236; 435/22, 23, 65, 412, 424, 435/430
See application file for complete search history.

(56) References Cited

U.S. PATENT DOCUMENTS

| | | | |
|---|---|---|---|
| 4,627,192 A | 12/1986 | Fick | |
| 4,948,811 A | 8/1990 | Spinner et al. | |
| 5,387,758 A | 2/1995 | Wong et al. | |
| 5,434,283 A | 7/1995 | Wong et al. | |
| 6,372,965 B1 | 4/2002 | Lightner et al. | ........... 800/293 |

FOREIGN PATENT DOCUMENTS

| | | |
|---|---|---|
| EP | 323 753 | 7/1989 |
| WO | WO 91/15578 | 10/1991 |
| WO | WO 93/11245 | 6/1993 |
| WO | WO 94/11516 | 5/1994 |

OTHER PUBLICATIONS

Conner et al., Coronary Heart Disease: Prevention, Complications, and Treatment, 43–46, 1985.
F.H. Mattson, *J. Am. Diet. Assoc.*, 89, 387–390, 1989.
Mensink et al., *New England J. Med.*, 321, 436–441, 1989.
S.M. Grundy, *New England J. Med.*, 314, 745–748, 1986.
Garg et al., *New England J. Med.*, 319, 829–834, 1988.
Williams et al., *J. Am. Assoc.*, 257, 3251–3256, 1987.
*Circulation*, vol. XLI, Suppl. I, Keys, A., ed., pp. I162–I183 (1970).
Pleines and Friedt, *Fat Sci. Technol.*, 90(5), 167–171, 1988.
Rakow and McGregor, *J. Amer. Oil Chem. Soc.*, 50, 400–403, Oct. 1973.
Roy and Tarr, *Pflansenzuchtg*, 95(3), 201–209, 1985.
Roy and Tarr, *Plant Breeding*, 98, 89–96, 1987.
Canvin, *Can. J. Botany*, 43, 63–69, 1965.
G.Z. Gaul, *Radiation Botany*, 4, 155–232, 1964.
G.Z. Rakow, *Pflanzenzuchtg*, 69, 62–82, 1973.
Scarth et al., *Can. J. Plant Sci.*, 68, 509–511, 1988.
Downey et al., *Can. J. Plant Sci.*, 43, 271, 1963.
B.R. Stefanson, In; High and Low Erucic Acid Rapeseed Oils, Ed. N.T. Kenthies, Academic Press Inc., Canada, 145–159, 1983.
G. Robbelen, In; Biotechnology for the Oils and Fats Industry, *American Oil Chemists Society*, 97–105, 1984.
Kirk–Othmer Encyclopedia of Chemical Technol., 3rd Edition, 9, 795–831, 1980.
Pleines et al., Abstract of Proceedings of the 7th International Rapeseed Congress, Pozman, Poland, May 11–14, 1987.
Tremolieres et al., *Phytochemistry*, 21(1), 41–45, 1982.
Robbelen et al., *Pflanzenauchtg*, 75, 93–105, 1985.
Robbelen et al., Proceedings of the International Conference on the Scientific, Technology, and Marketing of Rapeseed and Rapeseed Products, Sep. 20–23, 1970.
Pleines et al., Abstract of 43rd Lecture Meeting of Deutsche Gesellschaft fur Feltwissenschaft in Hamburg, Sep. 30–Oct. 11, 1987.
Brunklaus–Jung et al., *Plant Breeding*, 98, 9–16, 1987.
Hoffman et al., *Theor. Appl. Genet.*, 61, 225–232, 1982.
Kondra et al., Selection for Oleic, Linoleic and Linolenic Acid Content in $F_2$ Populations of Rape, *Can. J. Plant Sci.*, 56, 961–966, 1976.
Svalöf 1886–1986 Research and Results in Plant Breeding, pp. 173–184 LTs forlag, Stockholm.
Okuley et al., *Plant Cell*, 6:147–158, 1994.
Arondel et al., *Science*, 258:1153–1155, 1992.
Yadav et al., *Plant Physiol.*, 103:467–476, 1993.
Hitz et al., *Plant Physiol.*, 103:635–641, 1994.
Töpfer et al., *Science*, 268:681–686, 1995.
Shanklin et al., *Biochemistry*, 33:12787, 1994.
"The Multinational Brassica Genome Project" http:/www.brassica.info/genomesize.htm (Mar. 14, 2003).*

* cited by examiner

*Primary Examiner*—Elizabeth F. McElwain
(74) *Attorney, Agent, or Firm*—Fish & Richardson P.C.

(57) ABSTRACT

Plants are disclosed that contain a mutation in a delta-12 or delta-15 fatty acid desaturase gene. Preferred plants are rapeseed and sunflower plants. Plants carrying such mutant genes have altered fatty acid composition in seeds. In one embodiment, a plant contains a mutation in a region having the conserved motif His-Xaa-Xaa-His, found in delta-12 and delta-15 fatty acid desaturases. A preferred motif has the sequence His-Glu-Cys-Gly-His. A preferred mutation in this motif has the amino acid sequence His-Lys-Cys-Gly-His. Nucleic acid fragments are disclosed that comprise a sequence of at least 20 nucleotides from a mutant delta-12 or delta-15 fatty acid desaturase gene.

34 Claims, 1 Drawing Sheet

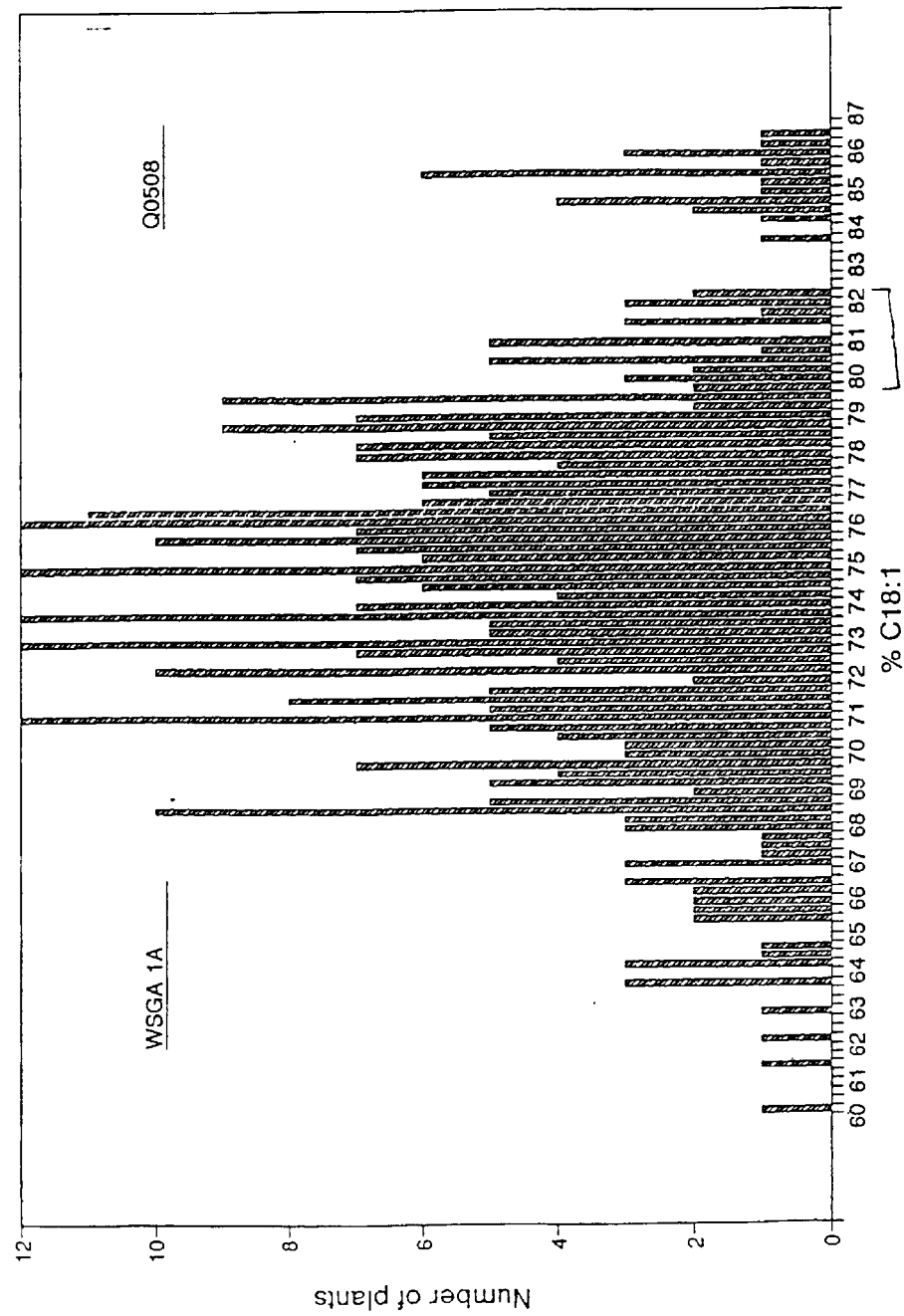
Fig. 1 C18:1 Frequencies for 92EF (WSGA 1A X Q0508)

BRASSICA OR HELIANTHUS PLANTS HAVING MUTANT DELTA-12 OR DELTA-15 SEQUENCES

CROSS REFERENCE TO RELATED APPLICATIONS

This application is a continuation-in-part of U.S. Ser. No. 08/416,497, filed Apr. 4, 1995, now U.S. Pat. No. 5,668,299, which is a continuation of U.S. Ser. No. 08/170,886, filed Dec. 21, 1993, now abandoned, which is a continuation-in-part of U.S. Ser. No. 07/739,965, filed Aug. 5, 1991, now abandoned, which is a continuation-in-part of U.S. Ser. No. 07/575,542, filed Aug. 30, 1990, now abandoned.

TECHNICAL FIELD

This invention relates to Brassica seeds and plants having mutant sequences which confer altered fatty acid profiles on the seed oil. More particularly, the invention relates to mutant delta-12 and delta-15 fatty acid desaturase sequences in such plants which confer such profiles.

BACKGROUND OF THE INVENTION

Diets high in saturated fats increase low density lipoproteins (LDL) which mediate the deposition of cholesterol on blood vessels. High plasma levels of serum cholesterol are closely correlated with atherosclerosis and coronary heart disease (Conner et al., Coronary Heart Disease: Prevention, Complications, and Treatment, pp. 43–64, 1985). By producing oilseed Brassica varieties with reduced levels of individual and total saturated fats in the seed oil, oil-based food products which contain less saturated fats can be produced. Such products will benefit public health by reducing the incidence of atherosclerosis and coronary heart disease.

The dietary effects of monounsaturated fats have also been shown to have dramatic effects on health. Oleic acid, the only monounsaturated fat in most edible vegetable oils, lowers LDL as effectively as linoleic acid, but does not affect high density lipoproteins (HDL) levels (Mattson, F. H., J. Am. Diet. Assoc., 89:387–391, 1989; Mensink et al., New England J. Med., 321:436–441, 1989). Oleic acid is at least as effective in lowering plasma cholesterol as a diet low in fat and high in carbohydrates (Grundy, S. M., New England J. Med., 314:745–748, 1986; Mensink et al., New England J. Med., 321:436–441, 1989). In fact, a high oleic acid diet is preferable to low fat, high carbohydrate diets for diabetics (Garg et al., New England J. Med., 319:829–834, 1988). Diets high in monounsaturated fats are also correlated with reduced systolic blood pressure (Williams et al., J. Am. Med. Assoc., 257:3251–3256, 1987). Epidemiological studies have demonstrated that the "Mediterranean" diet, which is high in fat and monounsaturates, is not associated with coronary heart disease (Keys, A., Circulation, 44(Suppl):1, 1970).

Many breeding studies have been conducted to improve the fatty acid profile of Brassica varieties. Pleines and Freidt, Fat Sci. Technol., 90(5), 167–171 (1988) describe plant lines with reduced $C_{18:3}$ levels (2.5–5.8%) combined with high oleic content (73–79%). Rakow and McGregor, J. Amer. Oil Chem. Soc., 50, 400–403 (October 1973) discuss problems associated with selecting mutants for linoleic and linolenic acids. In. Can. J. Plant Sci., 68, 509–511 (April 1988) Stellar summer rape producing seed oil with 3% linolenic acid and 28% linoleic acid is disclosed. Roy and Tarr, Z. Pflanzenzuchtg, 95(3), 201–209 (1985) teaches transfer of genes through an interspecific (gross from Brassica juncea into Brassica napus resulting in a reconstituted line combining high linoleic with low linolenic acid content. Roy and Tarr, Plant Breeding, 98, 89–96 (1987) discuss prospects for development of B. napus L. having improved linolenic and linolenic acid content. European Patent application 323,751 published Jul. 12, 1989 discloses seeds and oils having greater than 79% oleic acid combined with less than 3.5% linolenic acid. Canvin, Can. J. Botany, 43, 63–69 (1965) discusses the effect of temperature on the fatty acid composition of oils from several seed crops including rapeseed.

Mutations typically are induced with Extremely high doses of radiation and/or chemical mutagens (maul, H. Radiation Botany (1964) 4:155–232). High dose levels which exceed LD50, and typically reach LD90, led to maximum achievable mutation rates. In mutation breeding of Brassica varieties high levels of chemical mutagens alone or combined with radiation have induced a limited number of fatty acid mutations (Rakow, G. Z. Pflanzenzuchtg (1973) 69:62–82). The low α-linolenic acid mutation derived from the Rakow mutation breeding program did not have direct commercial application because of low seed yield. The first commercial cultivar using the low α-linolenic acid mutation derived in 1973 was released in 1988 as the variety Stellar (Scarth, R. et al., Can. J. Plant Sci. (1988) 68:509–511). Stellar was 20% lower yielding than commercial cultivars at the time of its release.

Canola-quality oilseed Brassica varieties with reduced levels of saturated fatty acids in the seed oil could be used to produce food products which promote cardiovascular health. Canola lines which are individually low in palmitic and stearic acid content or low in combination will reduce the levels of saturated fatty acids. Similarly, Brassica varieties with increased monounsaturate levels in the seed oil, and products derived from such oil, would improve lipid nutrition. Canola lines which are low in linoleic acid tend to have high oleic acid content, and can be used in the development of varieties having even higher oleic acid content.

Increased palmitic acid content provides a functional improvement in food applications. Oils high in palmitic acid content are particularly useful in the formulation of margarines. Thus, there is a need for manufacturing purposes for oils high in palmitic acid content.

Decreased α-linolenic acid content provides a functional improvement in food applications. Oils which are low in linolenic acid have increased stability. The rate of oxidation of lipid fatty acids increases with higher levels of linolenic acid leading to off-flavors and off-odors in foods. There is a need in the food industry for oils low in alpha linolenic acid.

Delta-12 fatty acid desaturase (also known as oleic desaturase) is involved in the enzymatic conversion of oleic acid to linoleic acid. Delta-15 fatty acid desaturase (also known as linoleic acid desaturase) is involved in the enzymatic conversion of linoleic acid to α-linolenic acid. A microsomal delta-12 desaturase has been cloned and characterized using T-DNA tagging. Okuley, et al., Plant Cell 6:147–158 (1994). The nucleotide sequences of higher plant genes encoding microsomal delta-12 fatty acid desaturase are described in Lightner et al., WO 94/11516. Sequences of higher plant genes encoding microsomal and plastid delta-15 fatty acid desaturases are disclosed in Yadav, N., et al., Plant Physiol., 103:467–476 (1993), WO 93/11245 and Arondel, V. et al., Science, 258:1353–1355 (1992). However, there are no teachings that disclose mutations in delta-12 or delta-15 fatty acid desaturase coding sequences from plants.

Furthermore, no methods have been described for developing plant lines that contain delta-12 or delta-15 fatty acid desaturase gene sequence mutations effective for altering the fatty acid composition of seeds.

SUMMARY OF THE INVENTION

The present invention comprises canola seeds, plant lines producing seeds, and plants producing seed, said seeds having a maximum content of FDA saturates of about 5% and a maximum erucic acid content of about 2% based upon total extractable oil and belonging to a line in which said saturates content has been stabilized for both the generation to which the seed belongs and its parent generation. Progeny of said seeds and canola, oil having a maximum erucic acid content of about 2%, based upon total extractable oil, are additional aspects of this invention. Preferred are seeds, plant lines producing seeds, and plants producing seeds, said seeds having an FDA saturates content of from about 4.2% to about 5.0% based upon total extractable oil.

The present invention further comprises Brassica seeds, plant lines producing seeds, and plants producing seeds, said seeds having a minimum oleic acid content of about 71% based upon total extractable oil and belonging to a line in which said oleic acid content has seen stabilized for both the generation to which the seed belongs and its parent generation. A further aspect of this invention is such high oleic acid seeds additionally having a maximum erucic acid content of about 2% based upon total extractable oil. Progeny of said seeds; and Brassica oil having 1) a minimum oleic acid content of about 71% or 2) a minimum oleic acid content of about 71% and a maximum erucic content of about 2% are also included in this invention. Preferred are seeds, plant lines producing seeds, and plants producing seeds, said seeds having an oleic acid content of from about 71.2% to about 78.3% based upon total extractable oil.

The present invention further comprises canola seeds, plant lines producing seeds, and plants producing seeds, said seeds having a maximum linoleic acid content of about 14% and a maximum erucic acid content of about 2% based upon total extractable oil and belonging to a line in which said acid content is stabilized for both the generation to which the seed belongs and its parent generation. Progeny of said seeds and canola oil having a maximum linoleic acid content of about 14% and a maximum erucic acid content of about 2%, are additional aspects of this invention. Preferred are seeds, plant lines producing seeds, and plants producing seeds, said seeds having a linoleic acid content of from about 8.4% to about 9.4% based upon total extractable oil.

The present invention further comprises Brassica seeds, plant lines producing seeds, and plants producing seeds, said seeds having a maximum palmitic acid content of about 3.5% and a maximum erucic acid content of about 2% based on total extractable oil and belonging to a line in which said acid content is stabilized for both the generation to which the seed belongs and its parent generation. Progeny of said seeds and canola having a maximum palmitic acid content of about 3.5% and a maximum erucic acid content of about 2%, are additional aspects of this invention. Preferred are seeds, plant lines producing seeds, and plants producing seeds, said seeds having a palmitic acid content of from about 2.7% to about 3.1% based upon total extractable oil.

The present invention further comprises Brassica seeds, plant lines producing seeds, and plants producing seeds, said seeds having a minimum palmitic acid content of about 9.0% based upon total extractable oil and belonging to a line in which said acid content is stabilized for both the generation to which the seed belongs and its parent generation. A further aspect of this invention is such high palmitic acid seeds additionally having a maximum erucic acid content of about 2% based upon total extractable oil. Progeny of said seeds; and Brassica oil having 1) a minimum palmitic acid content of about 9.0%, or 2) a minimum palmitic acid content of about 9.0% and a maximum erucic acid content of about 2% are also included in this invention. Preferred are seeds, plant lines producing seeds, and plants producing seeds, said seeds having a palmitic acid content of from about 9.1% to about 11.7% based upon total extractable oil.

The present invention further comprises Brassica seeds, plant lines producing seeds, and plants producing seeds, said seeds having a maximum stearic acid content of about 1.1% based upon total extractable oil and belonging to a line in which said acid content is stabilized for both the generation to which the seed belongs and its parent generation. Progeny of said seeds have a canola oil having a maximum stearic acid content of about 1.1% and maximum erucic acid content of about 2%. Preferred are seeds, plant lines producing seeds, and plants producing seeds having a palmitic acid content of from about 0.8% to about 1.1% based on total extractable oil.

The present invention further comprises Brassica seeds, plant lines producing seeds, and plants producing seeds, said seeds having a sum of linoleic acid content and linolenic acid content of a maximum of about 14% based upon total extractable oil and belonging to a line in which said acid content is stabilized for both the generation to which the seed belongs and its parent generation. Progeny of said seeds have a canola oil having a sum of linoleic acid content and linolenic acid content of a maximum of about 14% and a maximum erucic acid content of about 2%. Preferred are seeds, plant lines producing seeds, and plants producing seeds having a sum of linoleic acid content and linolenic acid content of from about 11.8% to about 12.5% based on total extractable oil.

The invention further comprises Brassicaceae or Helianthus seeds, plants and plant lines having at least one mutation that controls the levels of unsaturated fatty acids in plants. One embodiment of the invention is an isolated nucleic acid fragment comprising a nucleotide sequence encoding a mutant delta-12 fatty acid desaturase conferring increased levels of oleic acid when the fragment is present in a plant. A preferred sequence comprises a mutant sequence as shown in SEQ ID NO:3. Another embodiment of the invention is an isolated nucleic acid fragment comprising a nucleotide sequence encoding a mutant delta-15 fatty acid desaturase. A plant in this embodiment may be soybean, oilseed Brassica species, sunflower, castor bean or corn. The mutant sequence may be derived from, for example, a Brassica napus, Brassica rapa, Brassica juncea or Helianthus delta-12 or delta-15 gene.

Another embodiment of the invention involves a method of producing a Brassicaceae or Helianthus plant line comprising the steps of: (a) inducing mutagenesis in cells of a starting variety of a Brassicaceae or Helianthus species; (b) obtaining progeny plants from the mutagenized cells; (c) identifying progeny plants that contain a mutation in a delta-12 or delta-15 fatty acid desaturase gene; and (d) producing a plant line by selfing.

Yet another embodiment of the invention involves a method of producing plant lines containing altered levels of unsaturated fatty acids comprising: (a) crossing a first plant with a second plant having a mutant delta-12 or delta-15 fatty acid desaturase; (b) obtaining seeds from the cross of step (a); (c) growing fertile plants from such seeds; (d) obtaining progeny seed the plants of step (c); and (e) identifying those seeds among the progeny that have altered fatty acid composition. Suitable plants are soybean, rapeseed, sunflower, safflower, castor bean and corn. Preferred plants are rapeseed and sunflower.

The invention is also embodied in vegetable oil obtained from plants disclosed herein, which vegetable oil has an altered fatty acid composition.

BRIEF DESCRIPTION OF THE FIGURES

FIG. 1 is a histogram showing the frequency distribution of seed oil oleic acid ($C_{18:1}$) content in a segregating population of a Q508 X Westar cross. The bar labeled WSGA 1A represents the $C_{18:1}$ content of the Westar parent. The bar labeled Q508 represents the $C_{18:1}$ content of the Q508 parent.

DESCRIPTION OF THE PREFERRED EMBODIMENTS

The U.S. Food and Drug Administration defines saturated fatty acids as the sum of lauric ($C_{12:0}$), myristic ($C_{14:0}$), palmitic ($C_{16:0}$) and stearic ($C_{18:0}$) acids. The term "FDA saturates" as used herein means this above-defined sum. Unless total saturate content is specified, the saturated fatty acid values expressed here include only "FDA saturates."

All percent fatty acids herein are percent by weight of the oil of which the fatty acid is a component.

As used herein, a "line" is a group of plants that display little or no genetic variation between individuals for at least one trait. Such lines may be created by several generations of self-pollination and selection, or vegetative propagation from a single parent using tissue or cell culture techniques. As used herein, the term "variety" refers to a line which is used for commercial production.

The term "mutagenesis" refers to the use of a mutagenic agent to induce random genetic mutations within a population of individuals. The treated population, or a subsequent generation of that population, is then screened for usable trait(s) that result from the mutations. A "population" is any group of individuals that share a common gene pool. As used herein "$M_0$" is untreated seed. As used herein, "$M_1$" is the seed (and resulting plants) exposed to a mutagenic agent, while "$M_2$" is the progeny (seeds and plants) of self-pollinated $M_1$ plants, "$M_3$" is the progeny of self-pollinated $M_2$ plants, and "$M_4$" is the progeny of self-pollinated $M_3$ plants. "$M_5$" is the progeny of self-pollinated $M_4$ plants. "$M_6$", "$M_7$", etc. are each the progeny of self-pollinated plants of the previous generation. The term "selfed" as used herein means self-pollinated.

"Stability" or "stable" as used herein means that with respect to a given fatty acid component, the component is maintained from generation to generation for at least two generations and preferably at least three generations at substantially the same level, e.g., preferably ±5%. The method of invention is capable of creating lines with improved fatty acid compositions stable up to ±5% from generation to generation. The above stability may be affected by temperature, location, stress and time of planting. Thus, comparison of fatty acid profiles should be made from seeds produced under similar growing conditions. Stability may be measured based on knowledge (of prior generation.

Intensive breeding has produced Brassica plants whose seed oil contains less than 2% erucic acid. The same varieties have also been bred so that the defatted meal contains less than 30 μmol glucosinolates/gram. "Canola" as used herein refers to plant variety seed or oil which contains less than 2% erucic acid ($C_{22:1}$), and meal with less than 30 μmol glucosinolates/gram.

Applicants have discovered plants with mutations in a delta-12 fatty acid desaturase gene. Such plants have useful alterations in the fatty acid compositions of the seed oil. Such mutations confer, for example, an elevated oleic acid content, a decreased, stabilized linoleic acid content, or both elevated oleic acid and decreased, stabilized linoleic acid content.

Applicants have further discovered plants with mutations in a delta-15 fatty acid desaturase gene. Such plants have useful alterations in the fatty acid composition of the seed oil, e.g., a decreased, stabilized level of α-linolenic acid.

Applicants have further discovered isolated nucleic acid fragments comprising sequences that carry mutations within the coding sequence of delta-12 or delta-15 desaturases. The mutations confer desirable alterations in fatty acid levels in the seed oil of plants carrying such mutations. Delta-12 fatty acid desaturase is also known as omega-6 fatty acid desaturase and is sometimes referred to herein as 12-DES. Delta-15 fatty acid desaturase is also known as omega-3 fatty acid desaturase and is sometimes referred to herein as 15-DES.

A nucleic acid fragment of the invention contains a mutation in a microsomal delta-12 fatty acid desaturase coding sequence or in a microsomal delta-15 fatty acid desaturase coding sequence. Such a mutation renders the resulting desaturase gene product non-functional in plants, relative to the function of the gene product encoded by the wild-type sequence. The non-functionality of the 12-DES gene product can be inferred from the decreased level of reaction product (linoleic acid) and increased level of substrate (oleic acid) in plant tissues expressing the mutant sequence, compared to the corresponding levels in plant tissues expressing the wild-type sequence. The non-functionality of the 15-DES gene product can be inferred from the decreased level of reaction product (α-linolenic acid) and the increased level of substrate (linoleic acid) in plant tissues expressing the mutant sequence, compared to the corresponding levels in plant tissues expressing the wild-type sequence.

A nucleic acid fragment of the invention may comprise a portion of the coding sequence, e.g., at least 20 nucleotides, provided that the fragment contains at least one mutation in the coding sequence. In one embodiment, a nucleic acid fragment of the invention comprises the full length coding sequence of a mutant delta-12 or mutant delta-15 fatty acid desaturase.

A mutation in a nucleic acid fragment of the invention may be in any portion of the coding sequence that renders the resulting gene product non-functional. Suitable types of mutations include, without limitation, insertions of nucleotides, deletions of nucleotides, or transitions and transversions in the wild-type coding sequence. Such mutations result in insertions of one or more amino acids, deletions of one or more amino acids, and non-conservative amino acid substitutions in the corresponding gene product. In some embodiments, the sequence of a nucleic acid fragment may comprise more than one mutation or more than one type of mutation.

Insertion or deletion of amino acids in a coding sequence may, for example, disrupt the conformation of essential alpha-helical or beta-pleated sheet regions of the resulting gene product. Amino acid insertions or deletions may also disrupt binding or catalytic sites important for gene product activity. It is known in the art that the insertion or deletion of a larger number of contiguous amino acids is more likely to render the gene product non-functional, compared to a smaller number of inserted or deleted amino acids.

Non-conservative amino acid substitutions may replace an amino acid of one class with an amino acid of a different class. Non-conservative substitutions may make a substantial change in the charge or hydrophobicity of the gene product. Non-conservative amino acid substitutions may also make a substantial change in the bulk of the residue side chain, e.g., substituting an alanyl residue for a isoleucyl residue.

Examples of non-conservative substitutions include the substitution of a basic amino acid for a non-polar amino acid, or a polar amino acid for an acidic amino acid. Because there are only 20 amino acids encoded in a gene, substitutions that result in a non-functional gene product may be determined by routine experimentation, incorporating amino acids of a different class in the region of the gene product targeted for mutation.

Preferred mutations are in a region of the nucleic acid having an amino acid sequence motif that is conserved among delta-12 fatty acid desaturases or delta-15 fatty acid desaturases, such as a His-Xaa-Xaa-Xaa-His motif (Tables 1–3). An example of a suitable region has a conserved HECGH motif that is found, for example, in nucleotides corresponding to amino acids 105 to 109 of the Arabidopsis and Brassica delta-12 desaturase sequences, in nucleotides corresponding to amino acids 101 to 105 of the soybean delta-12 desaturase sequence and in nucleotides corresponding to amino acids 111 to 115 of the maize delta-12 desaturase sequence (Table 1). See e.g., WO 94/11516; Okuley et al., Plant Cell 6:147–158 (1994). The one letter amino acid designations used herein are described in Alberts, B. et al., Molecular Biology of the Cell, 3rd edition, Garland Publishing, New York, 1994. Amino acids flanking this motif are also highly conserved among delta-12 and delta-15 desaturases and are also suitable candidates for mutations in fragments of the invention. An illustrative embodiment of a mutation in a nucleic acid fragment of the invention is a Glu to Lys substitution in the HECGH motif of a Brassica microsomal delta-12 desaturase sequence, either the D form or the F form. This mutation results in the sequence HECGH being changed to HKCGH as seen by comparing SEQ ID NO:6 (wild-type D form) to SEQ ID NO:8 (mutant D form).

A similar motif may be found at amino acids 101 to 105 of the Arabidopsis microsomal delta-15 fatty acid desaturase, as well as in the corresponding rape and soybean desaturases (Table 5). See, e.g., WO 93/11245; Arondel, V. et al., Science, 258:1153–1155 (1992); Yadav, N. et al., Plant Physiol., 103:467–476 (1993). Plastid delta-15 fatty acids have a similar motif (Table 5).

Among the types of mutations in an HECGH motif that render the resulting gene product non-functional are non-conservative substitutions. An illustrative example of a non-conservative substitution is substitution of a glycine residue for either the first or second histidine. Such a substitution replaces a polar residue (histidine) with a non-polar residue (glycine). Another type of mutation that renders the resulting gene product non-functional is an insertion mutation, e.g., insertion of a glycine between the cystine and glutamic acid residues in the HECGH motif.

Other regions having suitable conserved amino acid motifs include the HRRHH motif shown in Table 2, the HRTHH motif shown in Table 6 and the HVAHH motif shown in Table 3. See, e.g., WO 94/11516; Hitz, W. et al., Plant Physiol., 105:635–641 (1994); Okuley, J., et al., Supra; and Yadav, N. et al., supra.

Another region suitable for a mutation in a delta-12 desaturase sequence contains the motif KYLNNP at nucleotides corresponding to amino acids 171 to 175 of the Brassica desaturase sequence (Table 4). An illustrative example of a mutation is this region is a Leu to His substitution, resulting in the amino acid sequence KYHNN (Compare wild-type SEQ ID NO:6 to mutant SEQ ID NO:8)

TABLE 1

Alignment of Amino Acid Sequences from Microsomal Delta-12 Fatty Acid Desaturases

| Species | Position | Amino Acid Secquence |
| --- | --- | --- |
| Arabidopsis thaliana | 100–129 | IWVIAHECGH HAFSDYQWLD DTVGLIFHSF |
| Glycine max | 96–125 | VWVIAHECGH HAFSKYQWVD DVVGLTLHST |
| Zea mays | 106–135 | VWVIAHECGH HAFSDYSLLD DVVGLVLHSS |
| Ricinus communis[a] | 1–29 | WVMAHDCGH HAFSDYQLLD DVVGLILHSC |
| Brassica napus D | 100–128 | VWVIAHECGH HAFSDYQWLD DTVGLIFHS |
| Brassica napus F | 100–128 | VWVIAHECGH HAFSDYQWLD DTVGLIFHS |

[a]from plasmid pRF2-1C

TABLE 2

Alignment of Amino Acid Sequences from Microsomal Delta-12 Fatty Acid Desaturases

| Species | Position | Amino Acid Sequence |
| --- | --- | --- |
| Arabidopsis thaliana | 130–158 | LLVPYFSWKY SHRRHHSNTG SLERDEVFV |
| Glycine max | 126–154 | LLVPYFSWKI SHRRHHSNTG SLDRDEVFV |
| Zea mays | 136–164 | LMVPYFSWKY SHRRHHSNTG SLERDEVFV |
| Ricinus Communis[a] | 30–58 | LLVPYFSWKH SHRRHHSNTG SLERDEVFV |
| Brassica napus D | 130–158 | LLVPYFSWKY SHRSHHSNTG SLERDEVFV |
| Brassica napus F | 130–158 | LLVPYFSWKY SHRRHHSNTG SLERDEVFV |

[a]from plasmid pRF2-1C

TABLE 3

Alignment of Amino Acid Sequences from Microsomal Delta-12 Fatty Acid Desaturases

| Species | Position | Amino Acid Sequence |
|---|---|---|
| Arabidopsis thaliana | 298–333 | DRDYGILNKV FHNITDTHVA HHLFSTMPHY NAMEAT |
| Glycine max | 294–329 | DRDYGILNKV FHHITDTHVA HHLFSTMPHY HAMEAT |
| Zea mays | 305–340 | DRDYGILNRV FHNITDTHVA HHLFSTMPHY HAMEAT |
| Ricinus communis[a] | 198–224 | DRDYGILNKV FHNITDTQVA HHLF TMP |
| Brassica napus D | 299–334 | DRDYGILNKV FHNITDTHVA HHPFSTMPHY HAMEAT |
| Brassica napus F | 299–334 | DRDYGILNKV FHNITDTHVA HHLFSTMPHY HAMEAT |

[a] from plasmid pRF2-1C

TABLE 4

Alignment of Conserved Amino Acids from Microsomal Delta-12 Fatty Acid Desaturases

| Species | Position | Amino Acid Sequence |
|---|---|---|
| Arabidopsis thaliana | 165–180 | IKWYGKYLNN PLGRIM |
| Glycine max | 161–176 | VAWFSLYLNN PLGRAV |
| Zea mays | 172–187 | PWYTPYVYNN PVGRVV |
| Ricinus Communis[a] | 65–80 | IRWYSKYLNN PPGRIM |
| Brassica napus D | 165–180 | IKWYGKYLNN PLGRTV |
| Brassica napus F | 165–180 | IKWYGKYLNN PLGRTV |

[a] from plasmid pRF2-1C

TABLE 5

Alignment of Conserved Amino Acids from Plastid and Microsomal Delta-15 Fatty Acid Desaturases

| Species | Position | Amino Acid Sequence |
|---|---|---|
| Arabidopsis thaliana[a] | 156–177 | WALFVLGHD CGHGSFSNDP KLN |
| Brassica napus[a] | 114–135 | WALFVLGHD CGHGSFSNDP RLN |
| Glycine max[a] | 164–185 | WALFVLGHD CGHGSFSNNS KLN |
| Arabidopsis thaliana | 94–115 | WAIFVLGHD CGHGSFSDIP LLN |
| Brassica napus | 85–106 | WAIFVLGHD CGHGSFSDIP LLN |
| Glycine max | 93–114 | WALFVLGHD CGHGSFSDSP PLN |

[a] Plastid sequences

The conservation of amino acid motifs and their relative positions indicates that regions of a delta-12 or delta-15 fatty acid desaturase that can be mutated in one species to generate a non-functional desaturase can be mutated in the corresponding region from other species to generate a non-functional 12-DES or 15-DES gene product in that species.

Mutations in any of the regions of Tables 1–6 are specifically included within the scope of the invention, provided that such mutation (or mutations) renders the resulting desaturase gene product non-functional, as discussed hereinabove.

A nucleic acid fragment containing a mutant sequence can be generated by techniques known to the skilled artisan. Such techniques include, without limitation, site-directed mutagenesis of wild-type sequences and direct synthesis using automated DNA synthesizers.

A nucleic acid fragment containing a mutant sequence can also be generated by mutagenesis of plant seeds or regenerable plant tissue by, e.g., ethyl methane sulfonate, X-rays or other mutagens. With mutagenesis, mutant plants having the desired fatty acid phenotype in seeds are identified by known techniques and a nucleic acid fragment containing the desired mutation is isolated from genomic DNA or RNA of the mutant line. The site of the specific mutation is then determined by sequencing the coding region of the 12-DES or 15-DES gene. Alternatively, labeled nucleic acid probes that are specific for desired mutational events can be used to rapidly screen a mutagenized population.

Seeds of Westar, a Canadian (Brassica napus) spring canola variety, were subjected to chemical mutagenesis. Mutagenized seeds were planted in the greenhouse and the plants were self-pollinated. The progeny plants were individually analyzed for fatty acid composition, and regrown either in the greenhouse or in the field. After four successive generations of self-pollinations, followed by chemical analysis of the seed oil at each cycle, several lines were shown to carry stably inherited mutations in specific fatty acid components, including reduced palmitic acid ($C_{16:0}$), increased palmitic acid, reduced stearic acid ($C_{18:0}$), increased oleic acid ($C_{18:1}$), reduced linoleic acid ($C_{18:2}$) and reduced linolenic acid ($C_{18:3}$), in the seed oil.

The general experimental scheme for developing lines with stable fatty acid mutations is shown in Scheme I hereinafter.

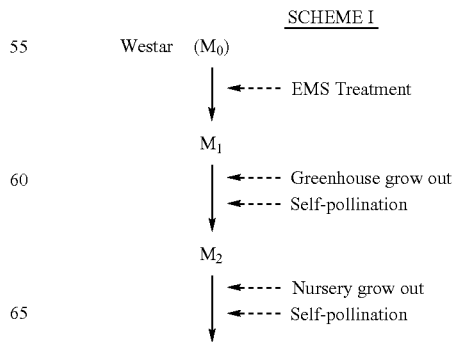

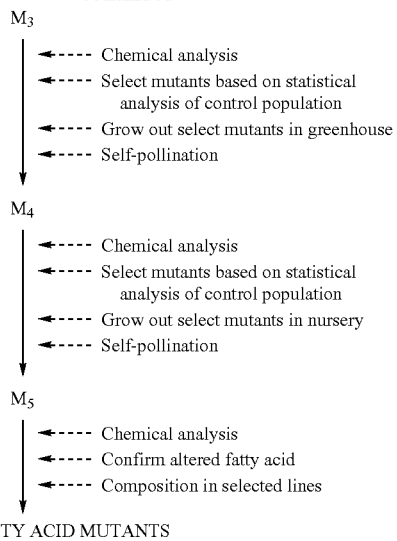

STABLE FATTY ACID MUTANTS

Westar seeds ($M_0$) were mutagenized with ethylmethanesulfonate (EMS). Westar is a registered Canadian spring variety with canola quality. The fatty acid composition of field-grown Westar, 3.9% $C_{16:0}$, 1.9% $C_{18:0}$, 67.5% $C_{18:1}$, 17.6% $C_{18:2}$, 7.4% $C_{18:3}$, <2% C20:1+$C_{22:1}$, has remained stable under commercial production, with <±10% deviation, since 1982. The disclosed method may be applied to all oilseed Brassica species, and to both Spring and Winter maturing types within each species. Physical mutagens, including but not limited to X-rays, UV rays, and other physical treatments which cause chromosome damage, and other chemical mutagens, including but not limited to ethidium bromide, nitrosoguanidine, diepoxybutane etc. may also be used to induce mutations. The mutagenesis treatment may also be applied to other stages of plant development, including but not limited to cell cultures, embryos, microspores and shoot apices. The $M_1$ seeds were planted in the greenhouse and $M_1$ plants were individually self-pollinated.

$M_2$ seed was harvested from the greenhouse and planted in the field in a plant-to-row design. Each plot contained six rows, and five $M_2$ lines were planted in each plot. Every other plot contained a row of non-mutagenized Westar as a control. Based on gas chromatographic analysis of $M_2$ seed, those lines which had altered fatty acid composition were self-pollinated and individually harvested.

$M_3$ seeds were evaluated for mutations on the basis of a Z-distribution. An extremely stringent 1 in 10,000 rejection rate was employed to establish statistical thresholds to distinguish mutation events from existing variation. Mean and standard deviation values were determined from the non-mutagenized Westar control population in the field. The upper and lower statistical thresholds for each fatty acid were determined from the mean value of the population±the standard deviation, multiplied by the Z-distribution. Based on a population size of 10,000, the confidence interval is 99.99%.

Seeds ($M_3$) from those $M_2$ lines which exceeded either the upper or lower statistical thresholds were replanted in the greenhouse and self-pollinated. This planting also included Westar controls. The $M_4$ seed was re-analyzed using new statistical thresholds established with a new control population. Those $M_4$ lines which exceeded the new statistical thresholds for selected fatty acid compositions were advanced to the nursery. Following self-pollination, $M_5$ seed from the field were re-analyzed once again for fatty acid composition. Those lines which remained stable for the selected fatty acids were considered stable mutations.

"Stable mutations" as used herein are (defined as $M_5$ or more advanced lines which maintain a selected altered fatty acid profile for a minimum of three generations, including a minimum of two generations under field conditions, and exceeding established statistical thresholds for a minimum of two generations, as determined by gas chromatographic analysis of a minimum of 10 randomly selected seeds bulked together. Alternatively, stability may be measured in the same way by comparing to subsequent generations. In subsequent generations, stability is defined as having similar fatty acid profiles in the seed as that of the prior or subsequent generation when grown under substantially similar conditions.

The amount of variability for fatty acid content in a seed population is quite significant when single seeds are analyzed. Randomly selected single seeds and a ten seed bulk sample of a commercial variety were compared. Significant variation among the single seeds was detected (Table A). The half-seed technique (Downey, R. K. and B. L. Harvey, Can. J. Plant Sci., 43:271 [1963]) in which one cotyledon of the germinating seed is analyzed or fatty acid composition and the remaining embryo grown into a plant has been very useful to plant breeding work to select individuals in a population for further generation analysis. The large variation seen in the single seed analysis (Table A) is reflected in the half-seed technique.

TABLE A

| | Single Seed Analysis for Fatty Acid Composition[1] | | | | | | | | | |
|---|---|---|---|---|---|---|---|---|---|---|
| SAMPLE | 16:0 | 16:1 | 18:0 | 18:1 | 18:2 | 18:3 | 20:0 | 20:1 | 22:0 | 22:1 |
| Bulk | 3.2 | 0.4 | 1.8 | 20.7 | 13.7 | 9.8 | 0.8 | 11.2 | 0.4 | 32.2 |
| 1 | 2.8 | 0.2 | 1.1 | 14.6 | 14.6 | 11.1 | 0.8 | 9.8 | 0.7 | 38.2 |
| 2 | 3.3 | 0.2 | 1.3 | 13.1 | 14.4 | 11.7 | 0.9 | 10.5 | 0.7 | 37.0 |
| 3 | 3.0 | — | 1.2 | 12.7 | 15.3 | 10.6 | 0.8 | 7.3 | 0.7 | 43.2 |
| 4 | 2.8 | 0.2 | 1.1 | 16.7 | 13.2 | 9.1 | 0.8 | 11.2 | 0.4 | 38.9 |
| 5 | 3.0 | — | 1.8 | 15.2 | 13.3 | 8.4 | 1.3 | 8.7 | 0.9 | 42.3 |
| 6 | 3.1 | — | 1.3 | 14.4 | 14.6 | 10.3 | 1.0 | 10.9 | 0.8 | 39.3 |
| 7 | 2.6 | — | 1.2 | 15.7 | 13.8 | 9.9 | 0.9 | 12.2 | 0.5 | 37.0 |
| 8 | 3.1 | — | 1.1 | 16.2 | 13.4 | 10.6 | 0.6 | 9.2 | 0.8 | 41.4 |
| 9 | 2.7 | 0.1 | 1.0 | 13.5 | 11.2 | 11.3 | 0.8 | 6.2 | 0.7 | 46.9 |
| 10 | 3.4 | 0.2 | 1.4 | 13.9 | 17.5 | 10.8 | 1.1 | 10.0 | 0.9 | 36.2 |

TABLE A-continued

Single Seed Analysis for Fatty Acid Composition[1]

| SAMPLE | 16:0 | 16:1 | 18:0 | 18:1 | 18:2 | 18:3 | 20:0 | 20:1 | 22:0 | 22:1 |
|---|---|---|---|---|---|---|---|---|---|---|
| 11 | 2.8 | 0.2 | 1.2 | 12.7 | 12.9 | 10.3 | 1.0 | 7.9 | 0.9 | 43.3 |
| 12 | 2.3 | 0.1 | 1.6 | 20.7 | 14.8 | 6.5 | 1.1 | 12.5 | 0.8 | 34.5 |
| 13 | 2.6 | 0.2 | 1.3 | 21.0 | 11.4 | 7.6 | 1.0 | 11.6 | 0.6 | 36.7 |
| 14 | 2.6 | 0.1 | 1.2 | 14.7 | 13.2 | 9.4 | 0.9 | 10.1 | 0.8 | 40.8 |
| 15 | 2.9 | 0.2 | 1.4 | 16.6 | 15.1 | 11.2 | 0.7 | 9.1 | 0.3 | 36.1 |
| 16 | 3.0 | 0.2 | 1.1 | 12.4 | 13.7 | 10.4 | 0.9 | 8.7 | 0.8 | 42.7 |
| 17 | 2.9 | 0.1 | 1.1 | 21.1 | 12.3 | 7.1 | 0.8 | 12.4 | 0.5 | 36.8 |
| 18 | 3.1 | 0.1 | 1.2 | 13.7 | 13.1 | 10.4 | 1.0 | 8.8 | 0.7 | 41.6 |
| 19 | 2.7 | 0.1 | 1.0 | 11.1 | 13.4 | 11.7 | 0.8 | 7.9 | 0.8 | 43.5 |
| 20 | 2.3 | 0.2 | 0.2 | 18.2 | 13.9 | 8.2 | 0.9 | 10.3 | 0.8 | 38.2 |
| Average | 2.8 | 0.2 | 1.2 | 15.4 | 13.8 | 9.8 | 0.9 | 9.8 | 0.7 | 39.7 |
| Minimum | 2.3 | 0.1 | 0.2 | 11.1 | 11.2 | 6.5 | 0.6 | 6.2 | 0.3 | 34.5 |
| Maximum | 3.4 | 0.2 | 1.8 | 21.1 | 17.5 | 11.7 | 1.3 | 12.5 | 0.9 | 46.9 |
| Range | 1.1 | 0.1 | 1.6 | 9.9 | 6.3 | 5.3 | 0.7 | 6.4 | 0.6 | 12.4 |

[1]Values expressed as percent of total oil

Plant breeders using the half-seed technique have found it unreliable in selecting stable genetically controlled fatty acid mutations (Stefanson, B. R., In; High and Low Erucic Acid Rapeseed Oils, Ed. N. T. Kenthies, Academic Press, Inc., Canada (1983) pp. 145–159). Although valuable in selecting individuals from a population, the selected traits are not always transmitted to subsequent generations (Rakow, G. and McGregor, D. I., J. Amer. Oil Chem. Soc. (1973) 50:400–403. To determine the genetic stability of the selected plants several self-pollinated generations are required (Robelen, G. In: Biotechnology for the Oils and Fats Industry, Ed. C. Ratledge, P. Dawson and J. Rattray, American Oil Chemists Society (1984) pp. 97–105) with chemical analysis of a bulk seed sample.

Mutation breeding has traditionally produced plants carrying, in addition to the trait of interest, multiple, deleterious traits, e.g., reduced plant vigor and reduced fertility. Such traits may indirectly affect fatty acid composition, producing an unstable mutation; and/or reduce yield, thereby reducing the commercial utility of the invention. To eliminate the occurrence of deleterious mutations and reduce the load of mutations carried by the plant a low mutagen dose was used in the seed treatments to create an LD30 population. This allowed for the rapid selection of single gene mutations for fatty acid traits in agronomic backgrounds which produce acceptable yields.

Other than changes in the fatty acid composition of the seed oil, the mutant lines described here have normal plant phenotype when grown under field conditions, and are commercially useful. "Commercial utility" is defined as having a yield, as measured by total pounds of seed or oil produced per acre, within 15% of the average yield of the starting ($M_0$) canola variety grown in the same region. To be commercially useful, plant vigor and high fertility are such that the crop can be produced in this yield by farmers using conventional farming equipment, and the oil with altered fatty acid composition can be extracted using conventional crushing and extraction equipment.

The seeds of several different fatty acid lines have been deposited with the American Type Culture Collection and have the following accession numbers.

| Line | Accession No. | Deposit Date |
|---|---|---|
| A129.5 | 40811 | May 25, 1990 |
| A133.1 | 40812 | May 25, 1990 |
| A144.1 | 40813 | May 25, 1990 |
| A200.7 | 40816 | May 31, 1990 |
| M3032.1 | 75021 | June 7, 1991 |
| M3094.4 | 75023 | June 7, 1991 |
| M3052.6 | 75024 | June 7, 1991 |
| M3007.4 | 75022 | June 7, 1991 |
| M3062.8 | 75025 | June 7, 1991 |
| M3028.10 | 75026 | June 7, 1991 |
| IMC130 | 75446 | April 16, 1993 |

In some plant species or varieties more than one form of endogenous microsomal delta-12 desaturase may be found. In amphidiploids, each form may be derived from one of the parent genomes making up the species under consideration. Plants with mutations in both forms have a fatty acid profile that differs from plants with a mutation in only one form. An example of such a plant is Brassica napus line Q508, a doubly-mutagenized line containing a mutant F-form of a wild-type delta-12 desaturase (SEQ ID NO:1) and a mutant D-form of a wild-type delta-12 desaturase (SEQ ID NO:5).

Preferred host or recipient organisms for introduction of a nucleic acid fragment of the invention are the oil-producing species, such as soybean (Glycine max), rapeseed (e.g., Brassica napus, B. rapa and B. juncea), sunflower (Helianthus annus), castor bean (Ricinus communis), corn (Zea mays), and safflower (Carthamus tinctorius).

Plants according to the invention preferably contain an altered fatty acid profile. For example, oil obtained from seeds of such plants may have from about 69 to about 90% oleic acid, based on the total fatty acid composition of the seed. Such oil preferably has from about 74 to about 90% oleic acid, more preferably from about 80 to about 90% oleic acid. In some embodiments, oil obtained from seeds produced by plants of the invention may have from about 2.0% to about 5.0% saturated fatty acids, based on total fatty acid composition of the seeds. In some embodiments, oil obtained from seeds of the invention may be from about 1.0% to about 10.0% linoleic acid, or from about 0.5% to about 10.0% α-linolenic acid.

In one embodiment of the claimed invention, a plant contains both a 12-DES mutation and a 15-DES mutation. Such plants can have a fatty acid composition comprising very high oleic acid and very low alpha-linolenic acid levels. Mutations in 12-DES and 15-DES may be combined in a plant by making a genetic cross between 12-DES and 15-DES single mutant lines. A plant having a mutation in delta-12 fatty acid desaturase is crossed or mated with a second plant having a mutation in delta-15 fatty acid desaturase. Seeds produced from the cross are planted and the resulting plants are selfed in order to obtain progeny seeds. These progeny seeds are then screened in order to identify those seeds carrying both mutant genes.

Alternatively, a line possessing either a 12-DES or a 15-DES mutation can be subjected to mutagenesis to generate a plant or plant line having mutations in both 12-DES and 15-DES. For example, the IMC129 line has a mutation in the coding region ($Glu_{106}$ to $Lys_{106}$) of the D form of the microsomal delta-12 desaturase structural gene. Cells (e.g., seeds) of this line can be mutagenized to induce a mutation in a 15-DES gene, resulting in a plant or plant line carrying a mutation in a delta-12 fatty acid desaturase gene and a mutation in a delta-15 fatty acid desaturase gene.

Progeny includes descendants of a particular plant or plant line, e.g., seeds developed on an instant plant. Progeny of an instant plant include seeds formed on $F_1$, $F_2$, $F_3$, and subsequent generation plants, or seeds formed on $BC_1$, $BC_2$, $BC_3$ and subsequent generation plants.

Those seeds having an altered fatty acid composition may be identified by techniques known to the skilled artisan, e.g., gas-liquid chromatography (GLC) analysis of a bulked seed sample or of a single half-seed. Half-seed analysis is well known in the art to be useful because the viability of the embryo is maintained and thus those seeds having a desired fatty acid profile may be planted to from the next generation. However, half-seed analysis is also known to be an inaccurate representation of genotype of the seed being analyzed. Bulk seed analysis typically yields a more accurate representation of the fatty acid profile of a given genotype.

The nucleic acid fragments of the invention can be used as markers in plant genetic mapping and plant breeding programs. Such markers may include restriction fragment length polymorphism (RFLP), random amplification polymorphism detection (RAPD), polymerase chain reaction (PCR) or self-sustained sequence replication (3SR) markers, for example. Marker-assisted breeding techniques may be used to identify and follow a desired fatty acid composition during the breeding process. Marker-assisted breeding techniques may be used in addition to, or as an alternative to, other sorts of identification techniques. An example of marker-assisted breeding is the use of PCR primers that specifically amplify a sequence containing a desired mutation in 12-DES or 15-DES.

Methods according to the invention are useful in that the resulting plants and plant lines have desirable seed fatty acid compositions as well as superior agronomic properties compared to known lines having altered seed fatty acid composition. Superior agronomic characteristics include, for example, increased seed germination percentage, increased seedling vigor, increased resistance to seedling fungal diseases (damping off, root rot and the like), increased yield, and improved standability.

While the invention is susceptible to various modifications and alternative forms, certain specific embodiments thereof are described in the general methods and examples set forth below. For example the invention may be applied to all Brassica species, including *B. rapa, B. juncea,* and *B. hirta,* to produce substantially similar results. It should be understood, however, that these examples are not intended to limit the invention to the particular forms disclosed but, instead the invention is to cover all modifications, equivalents and alternatives falling within the scope of the invention. This includes the use of somaclonal variation; physical or chemical mutagenesis of plant parts; anther, microspore or ovary culture followed by chromosome doubling; or self- or cross-pollination to transmit the fatty acid trait, alone or in combination with other traits, to develop new Brassica lines.

EXAMPLE 1

Selection of Low FDA Saturates

Prior to mutagenesis, 30,000 seeds of *B. napus* cv. Westar seeds were preimbibed in 300-seed lots for two hours on wet filter paper to soften the seed coat. The preimbibed seeds were placed in 80 mM ethylmethanesulfonate (EMS) for four hours. Following mutagenesis, the seeds were rinsed three times in distilled water. The seeds were sown in 48-well flats containing Pro-Mix. Sixty-eight percent of the mutagenized seed germinated. The plants were maintained at 25° C./15° C., 14/10 hr day/night conditions in the greenhouse. At flowering, each plant was individually self-pollinated.

$M_2$ seed from individual plants were individually catalogued and stored, approximately 15,000 $M_2$ lines was planted in a summer nursery in Carman, Manitoba. The seed from each selfed plant were planted in 3-meter rows with 6-inch row spacing. Westar was planted as the check variety. Selected lines in the field were selfed by bagging the main raceme of each plant. At maturity, the selfed plants were individually harvested and seeds were catalogued and stored to ensure that the source of the seed was known.

Self-pollinated $M_3$ seed and Westar controls were analyzed in 10-seed bulk samples for fatty acid composition via gas chromatography. Statistical thresholds for each fatty acid component were established using a Z-distribution with a stringency level of 1 in 10,000. The selected $M_3$ seeds were planted in the greenhouse along with Westar controls. The seed was sown in 4-inch pots containing Pro-Mix soil and the plants were maintained at 25° C./15° C., 14/10 hr day/night cycle in the greenhouse. At flowering, the terminal raceme was self-pollinated by bagging. At maturity, selfed $M_4$ seed was individually harvested from each plant, labelled, and stored to ensure that the source of the seed was known.

The $M_4$ seed was analyzed in 10-seed bulk samples. Statistical thresholds for each fatty acid component were established from 259 control samples using a Z-distribution of 1 in 800. Selected $M_4$ lines were planted in a field trial in Carman, Manitoba in 3-meter rows with 6-inch spacing. Ten $M_4$ plants in each row were bagged for self-pollination. At maturity, the selfed plants were individually harvested and the open pollinated plants in the row were bulk harvested. The $M_5$ seed from single plant selections was analyzed in 10-seed bulk samples and the bulk row harvest in 50-seed bulk samples.

Selected $M_5$ lines were planted in the greenhouse along with Westar controls. The seed was grown as previously described. At flowering the terminal raceme was self-pollinated by bagging. At maturity, self ed $M_6$ seed was individually harvested from each plant and analyzed in 10-seed bulk samples for fatty acid composition.

Selected $M_6$ lines were entered into field trials in Eastern Idaho. The four trial locations were selected for the wide variability in growing conditions. The locations included Burley, Tetonia, Lamont and Shelley (Table I). The lines were planted in four 3-meter rows with an 8-inch spacing, each plot was replicated four times. The planting design was determined using a Randomized Complete Block Designed. The commercial cultivar Westar was used as a check cultivar. At maturity the plots were harvested to determine yield. Yield of the entries in the trial was determined by taking the statistical average of the four replications. The Least Significant Differences Test was used to rank the entries in the randomized complete block design.

TABLE I

Trial Locations for Selected Fatty Acid Mutants

| LOCATION | SITE CHARACTERIZATIONS |
|---|---|
| BURLEY | Irrigated. Long season. High temperatures during flowering. |
| TETONIA | Dryland. Short season. Cool temperatures. |
| LAMONT | Dryland. Short season. Cool temperatures. |
| SHELLEY | Irrigated. Medium season. High temperatures during flowering. |

To determine the fatty acid profile of entries, plants in each plot were bagged for self-pollination. The $M_7$ seed from single plants was analyzed for fatty acids in ten-seed bulk samples.

To determine the genetic relationships of the selected fatty acid mutants crosses were made. Flowers of $M_6$ or later generation mutations were used in crossing. $F_1$ seed was harvested and analyzed for fatty acid composition to determine the mode of gene action. The $F_1$ progeny were planted in the greenhouse. The resulting plants were self-pollinated, the $F_2$ seed harvested and analyzed for fatty acid composition for allelism studies. The $F_2$ seed and parent line seed was planted in the greenhouse individual plants were self-pollinated. The $F_3$ seed of individual plants was tested for fatty acid composition using 10-seed bulk samples as described previously.

In the analysis of some genetic relationships dihaploid populations were made from the microspores of the $F_1$ hybrids. Self-pollinated seed from dihaploid plants were analyzed for fatty acid analysis using methods described previously.

For chemical analysis, 10-seed bulk samples were hand ground with a glass rod in a 15-mL polypropylene tube and extracted in 1.2 mL 0.25 N KOH in 1:1 ether/methanol. The sample was vortexed for 30 sec. and heated for 60 sec. in a 60° C. water bath. Four mL of saturated NaCl and 2.4 mL of iso-octane were added, and the mixture was vortexed again. After phase separation, 600 µL of the upper organic phase were pipetted into individual vials and stored under nitrogen at −5° C. One µL samples were injected into a Supelco SP-2330 fused silica capillary column (0.25 mm ID, 30 M length, 0.20 µm df).

The gas chromatograph was set at 180° C. for 5.5 minutes, then programmed for a 2° C./minute increase to 212° C., and held at this temperature for 1.5 minutes. Total run time was 23 minutes. Chromatography settings were: Column head pressure—15 psi, Column flow (He)—0.7 mL/min., Auxiliary and Column flow—33 mL/min., Hydrogen flow—33 mL/min., Air flow—400 mL/min., Injector temperature—250° C., Detector temperature—300° C., Split vent—1/15.

Table II describes the upper and lower statistical thresholds for each fatty acid of interest.

TABLE II

Statistical Thresholds for Specific Fatty Acids Derived from Control Westar Plantings

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats* |
| $M_3$ Generation (1 in 10,000 rejection rate) | | | | | | |
| Lower | 3.3 | 1.4 | — | 13.2 | 5.3 | 6.0 |
| Upper | 4.3 | 2.5 | 71.0 | 21.6 | 9.9 | 8.3 |
| $M_4$ Generation (1 in 800 rejection rate) | | | | | | |
| Lower | 3.6 | 0.8 | — | 12.2 | 3.2 | 5.3 |
| Upper | 6.3 | 3.1 | 76.0 | 32.4 | 9.9 | 11.2 |
| $M_5$ Generation (1 in 755 rejection rate) | | | | | | |
| Lower | 2.7 | 0.9 | — | 9.6 | 2.6 | 4.5 |
| Upper | 5.7 | 2.7 | 80.3 | 26.7 | 9.6 | 10.0 |

*Sats = Total Saturate Content

At the $M_3$ generation, twelve lines exceeded the lower statistical threshold for palmitic acid ($\leq 3.3\%$). Line W13097.4 had 3.1% palmitic acid and an FDA saturate content of 4.5%. After a cycle in the greenhouse, $M_4$ seed from line W13097.4 (designated line A144) was analyzed. Line W13097.4.1(A144.1) had 3.1% $C_{16:0}$, exceeding the lower statistical threshold of 3.6%. The FDA saturate content for A144.1 was 4.5%. The fatty acid compositions for the $M_3$, $M_4$ and $M_5$ generations of this family are summarized in Table III.

TABLE III

Fatty Acid Composition of a Low Palmitic Acid/Low FDA Saturate Canola Line Produced by Seed Mutagenesis

| Genotype[a] | Percent Fatty Acids | | | | | | |
|---|---|---|---|---|---|---|---|
| | $C_{16:0}$ | $C_{18:0}$ | $C_{18:1}$ | $C_{18:2}$ | $C_{18:3}$ | Sats[b] | Tot Sat[c] |
| Westar | 3.9 | 1.9 | 67.5 | 17.6 | 7.4 | 5.9 | 7.0 |
| W13097.4 ($M_3$) | 3.1 | 1.4 | 63.9 | 18.6 | 9.5 | 4.5 | 5.6 |
| W13097.4 ($M_4$) | 3.1 | 1.4 | 66.2 | 19.9 | 6.0 | 4.5 | 5.5 |
| A144.1.9 ($M_5$) | 2.9 | 1.4 | 64.3 | 20.7 | 7.3 | 4.4 | 5.3 |

[a]Letter and numbers up to second decimal point indicate the plant line. Number after second decimal point indicates an individual plant.
[b]Sat = FDA Saturates
[c]Tot Sat = Total Saturate Content The $M_5$ seed of ten self-pollinated A144.1 (ATCC 40813) plants averaged 3.1% palmitic acid and 4.7% FDA saturates. One selfed plant (A144.1.9) contained 2.9% palmitic acid and FDA saturates of 4.4%. Bulk seed analysis from open-pollinated (A144.1) plants at the $M_5$ generation averaged 3.1% palmitic acid and 4.7% FDA saturates. The fatty acid composition of the bulked and individual A144.1 lines are summarized in Table IV.

TABLE IV

Fatty Acid Composition of A144
Low Palmitic Acid/Low FDA Saturate Line

| Gentotype[a] | Percent Fatty Acids | | | | | | |
|---|---|---|---|---|---|---|---|
| | $C_{16:0}$ | $C_{18:0}$ | $C_{18:1}$ | $C_{18:2}$ | $C_{18:3}$ | Sats[b] | Tot Sat[c] |
| Individually Self-Pollinated Plants | | | | | | | |
| A144.1.1 | 3.2 | 1.6 | 64.4 | 20.5 | 7.0 | 4.8 | 5.9 |
| A144.1.2 | 3.0 | 1.5 | 67.4 | 18.6 | 6.3 | 4.5 | 5.7 |
| A144.1.3 | 3.6 | 1.8 | 61.4 | 22.4 | 7.5 | 5.2 | 6.6 |
| A144.1.4 | 3.2 | 1.5 | 64.6 | 20.9 | 6.7 | 4.7 | 5.8 |
| A144.1.5 | 3.3 | 1.7 | 60.0 | 23.9 | 7.9 | 5.0 | 6.1 |
| A144.1.6 | 3.1 | 1.4 | 67.3 | 17.8 | 6.5 | 4.6 | 5.2 |
| A144.1.7 | 3.1 | 1.6 | 67.7 | 17.4 | 6.5 | 4.8 | 5.4 |
| A144.1.8 | 3.1 | 1.8 | 66.9 | 18.7 | 6.1 | 4.9 | 5.4 |
| A144.1.9 | 2.9 | 1.4 | 64.3 | 20.7 | 7.3 | 4.4 | 5.3 |
| A144.1.10 | 3.1 | 1.5 | 62.5 | 20.4 | 7.7 | 4.6 | 5.6 |
| Average of Individually Self-Pollinated Plants | | | | | | | |
| A144.1.1-10 | 3.1 | 1.6 | 64.8 | 20.1 | 6.9 | 4.7 | 5.7 |
| Bulk Analysis of Open-Pollinated Plants | | | | | | | |
| A144.1B | 3.1 | 1.6 | 64.8 | 19.4 | 7.8 | 4.7 | 5.7 |

[a]Letter and numbers up to second decimal point indicate the plant line. Number after second decimal point indicates an individual plant.
[b]Sat = FDA Saturates
[c]Tot Sat = Total Saturate Content These reduced levels have remained stable to the $M_7$ generations in both greenhouse and field conditions. These reduced levels have remained stable to the $M_7$ generation in multiple location field trails. Over all locations, the self-pollinated plants (A144) averaged 2.9% palmitic acid and FDA saturates of 4.6%. The fatty acid composition of the A144 lines for each Idaho location are summarized in Table V. In the multiple location replicated trial the yield of A144 was not significantly different in yield from the parent cultivar Westar. By means of seed mutagenesis, the level of saturated fatty acids of canola B. napus) was reduced from 5.9% to 4.6%. The palmitic acid content was reduced from 3.9% to 2.9%.

TABLE V

Fatty Acid Composition of a Mutant Low Palmitic
Acid/Low FDA Saturate Canola Line at
Different Field Locations in Idaho

| Trial Location | Percent Fatty Acids | | | | | | |
|---|---|---|---|---|---|---|---|
| | $C_{16:0}$ | $C_{18:0}$ | $C_{18:1}$ | $C_{18:2}$ | $C_{18:3}$ | Sats | Tot Sats |
| Burley | 2.9 | 1.3 | 62.3 | 20.6 | 10.3 | 4.2 | 5.0 |
| Tetonia | 2.9 | 1.7 | 59.7 | 21.0 | 11.2 | 4.6 | 5.7 |
| Lamont | 3.1 | 1.8 | 63.2 | 19.5 | 9.0 | 4.9 | 5.9 |
| Shelley | 2.8 | 1.9 | 64.5 | 18.8 | 8.8 | 4.7 | 5.9 |

To determine the genetic relationship of the palmitic acid mutation in A144 ($C_{16:0}$—3.0%, $C_{18:0}$—1.5%, $C_{18:1}$—67.4%, $C_{18:2}$—18.6%, $C_{18:3}$—6.3%) to other fatty acid mutations it was crossed to A129 a mutant high oleic acid ($C_{16:0}$—3.8%, $C_{18:0}$—2.3%, $C_{18:1}$—75.6%, $C_{18:2}$—9.5%, $C_{18:3}$—4.9%). Over 570 dihaploid progeny produced from the $F_1$ hybrid were harvested and analyzed for fatty acid composition. The results of the progeny analysis are summarized in Table VB. Independent segregation of the palmitic traits was observed which demonstrates that the genetic control of palmitic acid in A144 is different from the high oleic acid mutation in A129.

TABLE VB

Genetic Studies of Dihaploid Progeny of A144 X A129

| Genotype | $C_{16:0}$ Content (%) | Frequency Observed | Expected |
|---|---|---|---|
| p − p − p2 − p2 − | 3.0% | 162 | 143 |
| p + p + p2 − p2 − | 3.4% | 236 | 286 |
| p + p + p2 + p2 + | 3.8% | 175 | 143 |

EXAMPLE 2

An additional low FDA saturate line, designated A149.3 (ATCC 40814), was also produced by the method of Example 1. A 50-seed bulk analysis of this line showed the following fatty acid composition: $C_{16:0}$—3.6%, $C_{18:0}$—1.4%, $C_{18:1}$—65.5%, $C_{18:2}$—18.3%, $C_{18:3}$—8.2%, FDA Sats—5.0%, Total Sats—5.9%. This line has also stably maintained its mutant fatty acid composition to the $M_5$ generation. In a multiple location replicated trial the yield of A149 was not significantly different in yield from the parent cultivar Westar.

EXAMPLE 3

An additional low palmitic acid and low FDA saturate line, designated M3094.4 (ATCC 75023), was also produced by the method of Example 1. A 10-seed bulk analysis of this line showed the following fatty acid composition: $C_{16:0}$—2.7%, $C_{18:0}$—1.6%, $C_{18:1}$—66.6%, $C_{18:2}$—20.0%, $C_{18:3}$—6.1%, $C_{20:1}$—1.4%, $C_{22:1}$—0.0%, FDA Saturate—4.3%, Total Saturates—5.2%. This line has stably maintained its mutant fatty acid composition to the $M_5$ generation. In a single replicated trial the yield of M3094 was not significantly different in yield from the parent cultivar.

M3094.4 was crossed to A144, a low palmitic acid mutation (Example 1) for allelism studies. Fatty acid composition of the $F_2$ seed showed the two lines to be allelic. The mutational events in A144 and M3094, although different in origin, are in the same gene.

EXAMPLE 4

In the studies of Example 1, at the $M_3$ generation, 470 lines exceed the upper statistical threshold for palmitic acid ($\geq 4.3\%$). One $M_3$ line, W14538.6, contained 9.2% palmitic acid. Selfed progenies of this line, since designated M3007.4 (ATCC 75022), continued to exceed to the upper statistical threshold for high palmitic acid at both the $M_4$ and $M_5$ generations with palmitic acid levels of 11.7% and 9.1%, respectively. The fatty acid composition of this high palmitic acid mutant, which was stable to the $M_7$ generation under both field and greenhouse conditions, is summarized in Table VI.

TABLE VI

Fatty Acid Composition of a High Palmitic
Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats* |
| Westar | 3.9 | 1.9 | 67.5 | 17.6 | 7.4 | 7.0 |
| W114538.6 ($M_3$) | 8.6 | 1.6 | 56.4 | 20.3 | 9.5 | 10.2 |

TABLE VI-continued

Fatty Acid Composition of a High Palmitic
Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats* |
| M3007.2 ($M_4$) | 11.7 | 2.1 | 57.2 | 18.2 | 5.1 | 13.9 |
| M3007.4 ($M_6$) | 9.1 | 1.4 | 63.3 | 13.7 | 5.5 | 12.7 |

*Sats = Total Saturate Content

To determine the genetic relationship of the high palmitic mutation in M3007.4 to the low palmitic mutation in A144 (Example 1) crosses were made. The $F_2$ progeny were analyzed for fatty acid composition. The data presented in Table VIB shows the high palmitic group ($C_{16:0} > 7.0\%$) makes up one-quarter of the total population analyzed. The high palmitic acid mutation was controlled by one single gene mutation.

TABLE VIB

Genetic Studies of M3007 X A144

| Genotype | $C_{16:0}$ Content (%) | Frequency | |
|---|---|---|---|
| | | Observed | Expected |
| p – p – /p – hp – | <7.0 | 151 | 142 |
| hp – hp – | >7.0 | 39 | 47 |

An additional $M_3$ line, W4773.7, contained 4.5% palmitic acid. Selfed progenies of this line, since designated A200.7 (ATCC 40816), continued to exceed the upper statistical threshold for high palmitic acid in both the $M_4$ and $M_5$ generations with palmitic acid levels of 6.3% and 6.0%, respectively. The fatty acid composition of this high palmitic acid mutant, which was stable to the $M_7$ generation under both field and greenhouse conditions, is summarized in Table VII.

TABLE VII

Fatty Acid Composition of a High Palmitic
Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats* |
| Westar | 3.9 | 1.9 | 67.5 | 17.6 | 7.4 | 7.0 |
| W4773.7 ($M_3$) | 4.5 | 2.9 | 63.5 | 19.9 | 7.1 | 9.3 |
| M4773.7.7 ($M_4$) | 6.3 | 2.6 | 59.3 | 20.5 | 5.6 | 10.8 |
| A200.7.7 ($M_5$) | 6.0 | 1.9 | 60.2 | 20.4 | 7.3 | 9.4 |

*Sats = Total Saturate Content

EXAMPLE 5

Selection of Low Stearic Acid Canola Lines

In the studies of Example 1, at the $M_3$ generation, 42 lines exceeded the lower statistical threshold for stearic acid (<1.4%). Line W14859.6 had 1.3% stearic acid. At the $M_5$ generation, its selfed progeny (M3052.1) continued to fall within the lower statistical threshold for $C_{18:0}$ with 0.8% stearic acid. The fatty acid composition of this low stearic acid mutant, which was stable under both field and greenhouse conditions is summarized in Table VIII. In a single location replicated yield trial M3052.1 was not significantly different in yield from the parent cultivar Westar.

TABLE VIII

Fatty Acid Composition of a Low
Stearic Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 5.9 |
| W14859.6 ($M_3$) | 5.3 | 1.3 | 56.1 | 23.7 | 9.6 | 7.5 |
| M3052.1 ($M_4$) | 4.9 | 0.9 | 58.9 | 22.7 | 9.3 | 5.8 |
| M3052.6 ($M_5$) | 4.4 | 0.8 | 62.1 | 21.2 | 7.9 | 5.2 |

To determine the genetic relationship of the low stearic acid mutation of M3052.1 to other fatty acid mutations it was crossed to the low palmitic acid mutation A144 (Example 1). Seed from over 300 dihaploid progeny were harvested and analyzed for fatty acid composition. The results are summarized in Table VIIIB. Independent segregation of the palmitic acid and stearic acid traits was observed. The low stearic acid mutation was genetically different from the low palmitic acid mutations found in A144 and M3094.

TABLE VIIIB

Genetic Studies of M3052 X A144

| Genotype | $C_{16:0} + C_{18:0}$ Content (%) | Frequency | |
|---|---|---|---|
| | | Observed | Expected |
| p – p – s – s – | <4.9% | 87 | 77 |
| p – p – s – s – / p + p + s – s – | 4.0% < X < 5.6% | 152 | 154 |
| p + p + s + s + | >5.6% | 70 | 77 |

An additional $M_5$ line, M3051.10, contained 0.9% and 1.1% stearic acid in the greenhouse and field respectively. A ten-seed analysis of this line showed the following fatty acid composition: $C_{16:0}$—3.9%, $C_{18:0}$—1.1%, $C_{18:1}$—61.7%, $C_{18:2}$—23.0%, $C_{18:3}$—7.6%, FDA saturates—5.0%, Total Saturates—5.8%. In a single location replicated yield trial M3051.10 was not significantly different in yield from the parent cultivar Westar. M3051.10 was crossed to M3052.1 for allelism studies. Fatty acid composition of the $F_2$ seed showed the two lines to be allelic. The mutational events in M3051.10 and M3052.1 although different in origin were in the same gene.

An additional $M_5$ line, M3054.7, contained 1.0% and 1.3% stearic acid in the greenhouse and field respectively. A ten-seed analysis of this line showed the following fatty acid composition: $C_{16:0}$—4.0%, $C_{18:0}$—1.0%, $C_{18:1}$—66.5%, $C_{18:2}$—18:4%, $C_{18:3}$—7.2%, saturates—5.0%, Total saturates—6.1%. In a single location replicated yield trial M3054.7 was not significantly different in yield from the parent cultivar Westar. M3054.7 was crossed to M3052.1 for allelism studies. Fatty acid composition of the $F_2$ seed showed the two lines to be allelic. The mutational events in M3054.7, M3051.10 and M3052.1 although different in origin were in the same gene.

EXAMPLE 6

High Oleic Acid Canola Lines

In the studies of Example 1, at the $M_3$ generation, 31 lines exceeded the upper statistical threshold for oleic acid ($\geq 71.0\%$). Line W7608.3 had 71.2% oleic acid. At the $M_4$ generation, its selfed progeny (W7608.3.5, since designated A129.5) continued to exceed the upper statistical threshold for $C_{18:1}$ with 78.8% oleic acid. $M_5$ seed of five self-pollinated plants of line A129.5 (ATCC 40811) averaged 75.0% oleic acid. A single plant selection, A129.5.3 had 75.6% oleic acid. The fatty acid composition of this high oleic acid mutant, which was stable under both field and greenhouse conditions to the $M_7$ generation, is summarized in Table IX. This line also stably maintained its mutant fatty acid composition to the $M_7$ generation in field trials in multiple locations. Over all locations the self-pollinated plants (A129) averaged 78.3% oleic acid. The fatty acid composition of the A129 for each Idaho trial location are summarized in Table X. In multiple location replicated yield trials, A129 was not significantly different in yield from the parent cultivar Westar.

The canola oil of A129, after commercial processing, was found to have superior oxidative stability compared to Westar when measured by the Accelerated Oxygen Method (AOM), American Oil Chemists' Society Official Method Cd 12–57 for fat stability; Active Oxygen Method (revised 1989). The AOM of Westar was 18 AOM hours and for A129 was 30 AOM hours.

TABLE IX

Fatty Acid Composition of a High Oleic Acid Canola Line Produced by Seed Mutagenesis

| Genotype | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 7.0 |
| W7608.3 ($M_3$) | 3.9 | 2.4 | 71.2 | 12.7 | 6.1 | 7.6 |
| W7608.3.5 ($M_4$) | 3.9 | 2.0 | 78.8 | 7.7 | 3.9 | 7.3 |
| A129.5.3 ($M_5$) | 3.8 | 2.3 | 75.6 | 9.5 | 4.9 | 7.6 |

Sats = Total Saturate Content

TABLE X

Fatty Acid Composition of a Mutant High Oleic Acid Line at Different Field Locations in Idaho

| Location | Percent Fatty Acids | | | | | |
|---|---|---|---|---|---|---|
| | $C_{16:0}$ | $C_{18:0}$ | $C_{18:1}$ | $C_{18:2}$ | $C_{18:3}$ | Sats |
| Burley | 3.3 | 2.1 | 77.5 | 8.1 | 6.0 | 6.5 |
| Tetonia | 3.5 | 3.4 | 77.8 | 6.5 | 4.7 | 8.5 |
| Lamont | 3.4 | 1.9 | 77.8 | 7.4 | 6.5 | 6.3 |
| Shelley | 3.3 | 2.6 | 80.0 | 5.7 | 4.5 | 7.7 |

Sats = Total Saturate Content

The genetic relationship of the high oleic acid mutation A129 to other oleic desaturases was demonstrated in crosses made to commercial canola cultivars and a low linolenic acid mutation. A129 was crossed to the commercial cultivar Global ($C_{16:0}$—4.5% $C_{18:0}$—1.5%, $C_{18:1}$—62.9%, $C_{18:2}$—20.0%, $C_{18:3}$—7.3%). Approximately 200 $F_2$ individuals were analyzed for fatty acid composition. The results are summarized in Table XB. The segregation fit 1:2:1 ratio suggesting a single co-dominant gene controlled the inheritance of the high oleic acid phenotype.

TABLE XB

Genetic Studies of A129 X Global

| Genotype | $C_{18:0}$ Content (%) | Frequency | |
|---|---|---|---|
| | | Observed | Expected |
| od – od – | 77.3 | 43 | 47 |
| od – od + | 71.7 | 106 | 94 |
| od + od + | 66.1 | 49 | 47 |

A cross between A129 and IMC 01, a low linolenic acid variety ($C_{16:0}$—4.1%, $C_{18:0}$—1.9%, $C_{18:1}$—66.4%, $C_{18:2}$—18.1%, $C_{18:3}$—5.7%), was made to determine the inheritance of the oleic acid desaturase and linoleic acid desaturase. In the $F_1$ hybrids both the oleic acid and linoleic acid desaturase genes approached the mid-parent values indicating a co-dominant gene actions. Fatty acid analysis of the $F_2$ individuals confirmed a 1:2:1:2:4:2:1:2:1 segregation of two independent, co-dominant genes (Table XC). A line was selected from the cross of A129 and IMC01 and designated as IMC130 (ATCC deposit no. 75446) as described in U.S. patent application Ser. No. 08/425,108, incorporated herein by reference.

TABLE XC

Genetic Studies of A129 X IMC 01

| Genotype | Ratio | Frequency | |
|---|---|---|---|
| | | Observed | Expected |
| od – od – ld – ld – | 1 | 11 | 12 |
| od – od – ld – ld + | 2 | 30 | 24 |
| od – od – ld + ld + | 1 | 10 | 12 |
| od – od + ld – ld – | 2 | 25 | 24 |
| od – od + ld – ld + | 4 | 54 | 47 |
| od – od + ld + ld + | 2 | 18 | 24 |
| od + od + ld – ld – | 1 | 7 | 12 |
| od + od + ld – ld + | 2 | 25 | 24 |
| od + od + ld + ld + | 1 | 8 | 12 |

An additional high oleic acid line, designated A128.3, was also produced by the disclosed method. A 50-seed bulk analysis of this line showed the following fatty acid composition: $C_{16:0}$—3.5%, $C_{18:0}$—1.8%, $C_{18:1}$—77.3%, $C_{18:2}$—9.0%, $C_{18:3}$—5.6%, FDA Sats—5.3%, Total Sats—6.4%. This line also stably maintained its mutant fatty acid composition to the $M_7$ generation. In multiple locations replicated yield trials, A128 was not significantly different in yield from the parent cultivar Westar.

A129 was crossed to A128.3 for allelism studies. Fatty acid composition of the $F_2$ seed showed the two lines to be allelic. The mutational events in A129 and A128.3 although different in origin were in the same gene.

An additional high oleic acid line, designated M3028.-10 (ATCC 75026), was also produced by the disclosed method in Example 1. A 10-seed bulk analysis of this line showed the following fatty acid composition: $C_{16:0}$—3.5%, $C_{18:0}$—1.8%, $C_{18:1}$—77.3%, $C_{18:2}$—9.0%, $C_{18:3}$—5.6%, FDA Saturates—5.3%, Total Saturates—6.4%. In a single location replicated yield trial M3028.10 was not significantly different in yield from the parent cultivar Westar.

EXAMPLE 7

Low Linoleic Acid Canola

In the studies of Example 1, at the $M_3$ generation, 80 lines exceeded the lower statistical threshold for linoleic acid (≦13.2%). Line W12638.8 had 9.4% linoleic acid. At the $M_4$ and $M_5$ generations, its selfed progenies [W12638.8, since designated A133.1 (ATCC 40812)] continued to exceed the statistical threshold for low $C_{18:2}$ with linoleic acid levels of 10.2% and 8.4%, respectively. The fatty acid composition of this low linoleic acrid mutant, which was stable to the $M_7$ generation under both field and greenhouse conditions, is summarized in Table XI. In multiple location replicated yield trials, A133 was not significantly different in yield from the parent cultivar Westar. An additional low linoleic acid line, designated M3062.8 (ATCC 75025), was also produced by the disclosed method. A 10-seed bulk analysis of this line showed the following fatty acid composition: $C_{16:0}$—3.8%, $C_{18:0}$—2.3%, $C_{18:1}$—77.1%, $C_{18:2}$—8.9%, $C_{18:3}$—4.3%, FDA Sats—6.1%. This line has also stably maintained its mutant fatty acid composition in the field and greenhouse.

TABLE XI

Fatty Acid Composition of a Low Linolenic Acid Canola Line Produced by Seed Mutagenesis

| | Percent Fatty Acids | | | | | |
|---|---|---|---|---|---|---|
| Genotype[a] | $C_{16:0}$ | $C_{18:0}$ | $C_{18:1}$ | $C_{18:2}$ | $C_{18:3}$ | Sats[b] |
| Westar | 3.9 | 1.9 | 67.5 | 17.6 | 7.4 | 7.0 |
| W12638.8 ($M_3$) | 3.9 | 2.3 | 75.0 | 9.4 | 6.1 | 7.5 |
| W12638.8.1 ($M_4$) | 4.1 | 1.7 | 74.6 | 10.2 | 5.9 | 7.1 |
| A133.1.8 ($M_5$) | 3.8 | 2.0 | 77.7 | 8.4 | 5.0 | 7.0 |

[a]Letter and numbers up to second decimal point indicate the plant line. Number after second decimal point indicates an individual plant.
[b]Sats = Total Saturate Content

EXAMPLE 8

Low Linolenic and Linoleic Acid Canola

In the studies of Example 1, at the $M_3$ generation, 57 lines exceeded the lower statistical threshold for linolenic acid (≦5.3%). Line W14749.8 had 5.3% linolenic acid and 15.0% linoleic acid. At the $M_4$ and $M_5$ generations, its selfed progenies [W14749.8, since designated M3032 (ATCC 75021)] continued to exceed the statistical threshold for low $C_{18:3}$ with linolenic acid levels of 2.7% and 2.3%, respectively, and for a low sum of linolenic and linoleic acids with totals of 11.8% and 12.5% respectively. The fatty acid composition of this low linolenic acid plus linoleic acid mutant, which was stable to the $M_5$ generation under both field and greenhouse conditions, is summarized in Table XII. In a single location replicated yield trial M3032 was not significantly different in yield from the parent cultivar (Westar).

TABLE XII

Fatty Acid Composition of a Low Linolenic Acid Canola Line Produced by Seed Mutagenesis

| | Percent Fatty Acids | | | | | |
|---|---|---|---|---|---|---|
| Genotype | $C_{16:0}$ | $C_{18:0}$ | $C_{18:1}$ | $C_{18:2}$ | $C_{18:3}$ | Sats |
| Westar | 3.9 | 1.9 | 67.5 | 17.6 | 7.4 | 7.0 |
| W14749.8 ($M_3$) | 4.0 | 2.5 | 69.4 | 15.0 | 5.3 | 6.5 |

TABLE XII-continued

Fatty Acid Composition of a Low Linolenic Acid Canola Line Produced by Seed Mutagenesis

| | Percent Fatty Acids | | | | | |
|---|---|---|---|---|---|---|
| Genotype | $C_{16:0}$ | $C_{18:0}$ | $C_{18:1}$ | $C_{18:2}$ | $C_{18:3}$ | Sats |
| M3032.8 ($M_4$) | 3.9 | 2.4 | 77.9 | 9.1 | 2.7 | 6.4 |
| M3032.1 ($M_5$) | 3.5 | 2.8 | 80.0 | 10.2 | 2.3 | 6.5 |

Sats = Total Saturate Content

EXAMPLE 9

The high oleic acid mutation of A129 was introduced into different genetic backgrounds by crossing and selecting for fatty acid and agronomic characteristics. A129 (now renamed IMC 129) was crossed to Legend, a commercial spring *Brassica napus* variety. Legend has the following fatty acid composition: $C_{16:0}$—3.8%, $C_{18:0}$—2.1%, $C_{18:1}$—63.1%, $C_{18:2}$—17.8%, $C_{18:3}$—9.3%. The cross and progeny resulting from were coded as 89B60303.

The $F_1$ seed resulting from the cross was planted in the greenhouse and self-pollinated to produce $F_2$ seed. The $F_2$ seed was planted in the field for evaluation. Individual plants were selected in the field for agronomic characteristics. At maturity, the $F_3$ seed was harvested from each selected plant and analyzed for fatty acid composition.

Individuals which had fatty acid profiles similar to the high oleic acid parent (IMC 129) were advanced back to the field. Seeds ($F_3$) of selected individuals were planted in the field as selfing rows and in plots for preliminary yield and agronomic evaluations. At flowerings the $F_3$ plants in the selfing rows were self-pollinated. At maturity the $F_4$ seed was harvested from individual plants to determine fatty acid composition. Yield of the individual selections was determined from the harvested plots.

Based on fatty acid composition of the individual plants and yield and agronomic characteristics of the plots $F_4$ lines were selected and advanced to the next generation in the greenhouse. Five plants from each selected line were self-pollinated. At maturity the $F_5$ seed was harvested from each and analyzed for fatty acid composition.

The $F_5$ line with the highest oleic fatty profile was advanced to the field as a selfing row. The remaining $F_5$ seed from the five plants was bulked together for planting the yield plots in the field. At flowering, the $F_5$ plants in each selfing-row were self-pollinated. At maturity the $F_6$ self-pollinated seed was harvest from the selfing row to determine fatty acid composition and select for the high oleic acid trait. Yield of the individual selections was determined from the harvested plots.

Fifteen $F_6$ lines having the high oleic fatty profile of IMC 129 and the desired agronomic characteristics were advanced to the greenhouse to increase seed for field trialing. At flowering the $F_6$ plants were self-pollinated. At maturity the $F_7$ seed was harvested and analyzed for fatty acid composition. Three $F_7$ seed lines which had fatty acid profiles most similar to IMC 129 (Table XIII) were selected and planted in the field as selfing rows, the remaining seed was bulked together for yield trialing. The high oleic fatty acid profile of IMC 129 was maintained through seven generations of selection for fatty acid and agronomic traits in an agronomic background of *Brassica napus* which was different from the parental lines. Thus, the genetic trait from IMC 129 for high oleic acid can be used in the development of new high oleic *Brassica napus* varieties.

TABLE XIII

Fatty Acid Composition of Advanced Breeding Generation with High Oleic Acid Trait (IMC 129 X Legend)

| $F_7$ Selections of 89B60303 | Fatty Acid Composition (%) | | | | |
|---|---|---|---|---|---|
| | $C_{16:0}$ | $C_{18:0}$ | $C_{18:1}$ | $C_{18:2}$ | $C_{18:3}$ |
| 93.06194 | 3.8 | 1.6 | 78.3 | 7.7 | 4.4 |
| 93.06196 | 4.0 | 2.8 | 77.3 | 6.8 | 3.4 |
| 93.06198 | 3.7 | 2.2 | 78.0 | 7.4 | 4.2 |

The high oleic acid trait of IMC 129 was also introduced into a different genetic background by combining crossing and selection methods with the generation of dihaploid populations from the microspores of the $F_1$ hybrids. IMC 129 was crossed to Hyola 41, a commercial spring *Brassica napus* variety. Hyola 41 has the following fatty acid composition: $C_{16:0}$—3.8%, $C_{18:0}$—2.7%, $C_{18:1}$— 64.9%, $C_{18:2}$—16.2%, $C_{18:3}$—9.1%. The cross and progeny resulting from the cross were labeled 90DU.146.

The $F_1$ seed was planted from the cross and a dihaploid ($DH_1$) population was made from the $F_1$ microspores using standard procedures for *Brassica napus*. Each $DH_1$ plant was self-pollinated at flowering to produce $DH_1$ seed. At maturity the $DH_1$ seed was harvested and analyzed for fatty acid composition. $DH_1$ individuals which expressed the high oleic fatty acid profit of IMC 129 were advanced to the next generation in the greenhouse. For each individual selected five $DH_1$ seeds were planted. At flowering the $DH_2$ plants were self-pollinated. At maturity the $DH_2$ seed was harvested and analyzed for fatty acid composition. The $DH_2$ seed which was similar in fatty acid composition to the IMC 129 parent was advanced to the field as a selfing row. The remaining $DH_2$ seed of that group was bulked and planted in plots to determine yield and agronomic characteristics of the line. At flowering individual $DH_3$ plants in the selfing row were self-pollinated. At maturity the $DH_3$ seed was harvested from the individual plants to determine fatty acid composition. Yield of the selections was determined from the harvested plots. Based on fatty acid composition, yield and agronomic characteristics selections were advanced to the next generation in the greenhouse. The $DH_4$ seed produced in the greenhouse by self-pollination was analyzed for fatty acid composition. Individuals which were similar to the fatty acid composition of the IMC 129 parent were advanced to the field to test for fatty acid stability and yield evaluation. The harvested $DH_5$ seed from six locations maintained the fatty acid profile of the IMC 129 parent (Table XIV).

TABLE XIV

Fatty Acid Composition of Advanced Dihaploid Breeding Generation with High Oleic Acid Trait (IMC 129 X Hyola 41)

| DH5 of 90DU.146 at Multiple Locations | Fatty Acid Comnosition (%) | | | | |
|---|---|---|---|---|---|
| | $C_{16:0}$ | $C_{18:0}$ | $C_{18:1}$ | $C_{18:2}$ | $C_{18:3}$ |
| Aberdeen | 3.7 | 2.6 | 75.4 | 8.1 | 7.2 |
| Blackfoot | 3.3 | 2.4 | 75.5 | 8.8 | 7.5 |
| Idaho Falls | 3.7 | 3.1 | 75.0 | 7.5 | 8.1 |
| Rexberg | 3.9 | 3.7 | 75.3 | 7.0 | 6.5 |
| Swan Valley | 3.5 | 3.4 | 74.5 | 7.0 | 7.3 |
| Lamont | 3.9 | 2.8 | 72.0 | 10.1 | 8.4 |

EXAMPLE 10

Canola Line Q508

Seeds of the *B. napus* line IMC-129 were mutagenized with methyl N-nitrosoguanidine (MNNG). The MNNG treatment consisted of three parts: pre-soak, mutagen application, and wash. A 0.05 M Sorenson's phosphate buffer was used to maintain pre-soak and mutagen treatment pH at 6.1. Two hundred seeds were treated at one time on filter paper (Whatman #3M) in a petri dish (100 mm×15 mm). The seeds were pre-soaked in 15 mls of 0.05 M Sorenson's buffer, pH 6.1, under continued agitation for two hours. At the end of the pre-soak period, the buffer was removed from the plate.

A 10 mM concentration of MNNG in 0.05 M Sorenson's buffer, pH 6.1, was prepared prior to use. Fifteen ml of 10 m MNNG was added to the seeds in each plate. The seeds were incubated at 22° C.±3° C. in the dark under constant agitation for four (4) hours. At the end of the incubation period, the mutagen solution was removed.

The seeds were washed with three changes of distilled water at 10 minute intervals. The fourth wash was for thirty minutes. This treatment regime produced an LD60 population.

Treated seeds were planted in standard greenhouse potting soil and placed into an environmentally controlled greenhouse. The plants were grown under sixteen hours of light. At flowering, the racemes were bagged to produce selfed seed. At maturity, the M2 seed was harvested. Each M2 line was given an identifying number. The entire MNNG-treated seed population was designated as the Q series.

Harvested M2 seeds was planted in the greenhouse. The growth conditions were maintained as previously described. The racemes were bagged at flowering for selfing. At maturity, the selfed M3 seed was harvested and analyzed for fatty acid composition. For each M3 seed line, approximately 10–15 seeds were analyzed in bulk as described in Example 1.

High oleic-low linoleic M3 lines were selected from the M3 population using a cutoff of >82% oleic acid and <5.0% linoleic. From the first 1600 M3 lines screened for fatty acid composition, Q508 was identified. Table XV shows the fatty acid composition of Q508, Westar and IMC 129. The Q508 M3 generation was advanced to the M4 generation in the greenhouse. The M4 selfed seed maintained the selected high oleic-low linoleic acid phenotype (Table XVI).

Nine other M4 high-oleic low-linoleic lines were also identified: Q3603, Q3733, Q4249, Q6284, Q6601, Q6761, Q7415, Q4275, and Q6676. Some of these lines had good agronomic characteristics and an elevated oleic acid level in seeds of about 80% to about 84%.

TABLE XV

Fatty Acid Composition of A129 and High Oleic Acid M3 Mutant Q508

| Line # | 16:0 | 18:0 | 18:1 | 18:2 | 18:3 |
|---|---|---|---|---|---|
| A129* | 4.0 | 2.4 | 77.7 | 7.8 | 4.2 |
| Q508 | 3.9 | 2.1 | 84.9 | 2.4 | 2.9 |

*Fatty acid composition of A129 is the average of 50 self-pollinated plants grown with the M3 population $M_4$ generation Q508 plants had poor agronomic qualities in the field compared to Westar. Typical plants were slow growing relative to Westar, lacked early vegetative vigor, were short in stature, tended to be chlorotic and had short pods. The yield of Q508 was very low compared to Westar.

The $M_4$ generation Q508 plants in the greenhouse tended to be reduced in vigor compared to Westar. However, Q508 yields in the greenhouse were greater than Q508 yields in the field.

TABLE XVI

Fatty Acid Composition of Seed Oil from Greenhouse-Grown Q508, IMC129 and Westar.

| Line | 16:0 | 18:0 | 18:1 | 18:2 | 18:3 | FDA Sats |
|---|---|---|---|---|---|---|
| IMC129[a] | 4.0 | 2.4 | 77.7 | 7.8 | 4.2 | 6.4 |
| Westar[b] | 3.9 | 1.9 | 67.5 | 17.6 | 7.4 | >5.8 |
| Q508[c] | 3.9 | 2.1 | 84.9 | 2.4 | 2.9 | 6.0 |

[a]Average of 50 self-pollinated plants
[b]Data from Example 1
[c]Average of 50 self-pollinated plants $M_4$ generation Q508 plants were crossed to a dihaploid selection of Westar, with Westar serving as the female parent. The resulting F1 seed was termed the 92EF population. About 126 F1 individuals that appeared to have better agronomic characteristics than the Q508 parent were selected for selfing. A portion of the $F_2$ seed from such individuals was replanted in the field. Each F2 plant was selfed and a portion of the resulting F3 seed was analyzed for fatty acid composition. The content of oleic acid in $F_3$ seed ranged from 59 to 79%. No high oleic (>80%) individuals were recovered with good agronomic type.

TABLE XVII

| LOCATION | SITE CHARACTERISTICS |
|---|---|
| BURLEY | Irrigated. Long season. High temperatures during flowering. |
| TETONIA | Dryland. Short season. Cool temperatures. |
| LAMONT | Dryland. Short season. Cool temperatures. |
| SHELLEY | Irrigated. Medium season. High temperatures during flowering. |

Yield of the entries in the trial was determined by taking the statistical average of the four replications. The Least Significant Difference Test was used to rank the entries in the randomized complete block design.

A portion of the $F_2$ seed of the 92EF population was planted in the greenhouse to analyze the genetics of the Q508 line. $F_3$ seed was analyzed from 380 F2 individuals. The $C_{18:1}$ levels of $F_3$ seed from the greenhouse experiment is depicted in figure 3. The data were tested against the hypothesis that Q508 contains two mutant genes that are semi-dominant and additive: the original IMC129 mutation as well as one additional mutation. The hypothesis also assumes that homozygous Q508 has greater than 85% oleic acid and homozygous Westar has 62–67% oleic acid. The possible genotypes at each gene in a cross of Q508 by Westar may be designated as:

AA=Westar Fad2[a]
BB=Westar Fad2[b]
aa=Q508 Fad2[a−]
bb=Q508 Fad2[b−]

Assuming independent segregation, a 1:4:6:4:1 ratio of phenotypes is expected. The phenotypes of heterozygous plants are assumed to be indistinguishable and, thus, the data were tested for fit to a 1:14:1 ratio of homozygous Westar: heterozygous plants: homozygous Q508.

| Phenotypic Ratio | # of Westar Alleles | Genotype |
|---|---|---|
| 1 | 4 | AABB(Westar) |
| 4 | 3 | AABb,AaBB,AABb,AaBB |
| 6 | 2 | AaBb,AAbb,AaBb,AaBb,aaBB,AaBb |
| 4 | 1 | Aabb,aaBb,Aabb,aaBb |
| 1 | 0 | aabb (Q508) |

Using Chi-square analysis, the oleic acid data fit a 1:14:1 ratio. It was concluded that Q508 differs from Westar by two major genes that are semi-dominant and additive and that segregate independently. By comparison, the genotype of IMC129 is aaBB.

The fatty acid composition of representative F3 individuals having greater than 85% oleic acid in seed oil is shown in Table XVIII. The levels of saturated fatty acids are seen to be decreased in such plants, compared to Westar.

TABLE XVIII

92EF $F_3$ Individuals with >85% $C_{18:1}$ in Seed Oil

| F3 Plant Identifier | Fatty Acid Composition (%) | | | | | |
|---|---|---|---|---|---|---|
| | C16:0 | C18:0 | C18:1 | C18:2 | C18:3 | FDASA |
| +38068 | 3.401 | 1.582 | 85.452 | 2.134 | 3.615 | 4.983 |
| +38156 | 3.388 | 1.379 | 85.434 | 2.143 | 3.701 | 4.767 |
| +38171 | 3.588 | 1.511 | 85.289 | 2.367 | 3.425 | 5.099 |
| +38181 | 3.75 | 1.16 | 85.312 | 2.968 | 3.819 | 4.977 |
| +38182 | 3.529 | 0.985 | 85.905 | 2.614 | 3.926 | 4.56 |
| +38191 | 3.364 | 1.039 | 85.737 | 2.869 | 4.039 | 4.459 |
| +38196 | 3.557 | 1.182 | 85.054 | 2.962 | 4.252 | 4.739 |
| +38202 | 3.554 | 1.105 | 86.091 | 2.651 | 3.721 | 4.713 |
| +38220 | 3.093 | 1.16 | 86.421 | 1.931 | 3.514 | 4.314 |
| +38236 | 3.308 | 1.349 | 85.425 | 2.37 | 3.605 | 4.718 |
| +38408 | 3.617 | 1.607 | 85.34 | 2.33 | 3.562 | 5.224 |
| +38427 | 3.494 | 1.454 | 85.924 | 2.206 | 3.289 | 4.948 |
| +38533 | 3.64 | 1.319 | 85.962 | 2.715 | 3.516 | 4.959 |

EXAMPLE 11

Leaf and Root Fatty Acid Profiles of Canola Lines IMC-129, Q508, and Westar

Plants of Q508, IMC 129 and Westar were grown in the greenhouse. Mature leaves, primary expanding leaves, petioles and roots were harvested at the 6–8 leaf stage, frozen in liquid nitrogen and stored at −70° C. Lipid extracts were analyzed by GLC as described in Example 1. The fatty acid profile data are shown in Table XIX.

The data in Table XIX indicate that total leaf lipids in Q508 are higher in $C_{18:1}$ content than the $C_{18:2}$ plus $C_{18:3}$ content. The reverse is true for Westar and IMC 129. The difference in total leaf lipids between C508 and IMC129 is consistent with the hypothesis that a second Fad2 gene is mutated in Q508.

The $C_{16:3}$ content in the total lipid fraction was about the same for all three lines, suggesting that the plastid FadC gene product was not affected bag the Q508 mutations. To confirm that the FadC gene was not mutated, chloroplast lipids were separated and analyzed. No changes in chloroplast $C_{16:1}$, $C_{16:2}$ or $C_{16:3}$ fatty acids were detected in the three lines. The similarity in plastid leaf lipids among Q508, Westar and IMC129 is consistent with the hypothesis that the second mutation in Q508 affects a microsomal Fad2 gene and not a plastid FadC gene.

TABLE XIX

| | MATURE LEAF | | | EXPANDING LEAF | | | PETIOLE | | | ROOT | | |
|---|---|---|---|---|---|---|---|---|---|---|---|---|
| | West. | 129 | 3Q508 | West. | 129 | 3Q508 | West. | 129 | 3Q508 | West. | 129 | 3Q508 |
| 16:0 | 12.1 | 11.9 | 10.1 | 16.4 | 16.1 | 11.3 | 21.7 | 23.5 | 11.9 | 21.1 | 21.9 | 12.0 |
| 16:1 | 0.8 | 0.6 | 1.1 | 0.7 | 0.6 | 1.1 | 1.0 | 1.3 | 1.4 | — | — | — |
| 16:2 | 2.3 | 2.2 | 2.0 | 2.8 | 3.1 | 2.8 | 1.8 | 2.2 | 1.8 | — | — | — |
| 16:3 | 14.7 | 15.0 | 14.0 | 6.3 | 5.4 | 6.9 | 5.7 | 4.6 | 5.7 | — | — | — |
| 18:0 | 2.2 | 1.6 | 1.2 | 2.5 | 2.8 | 1.6 | 3.7 | 4.0 | 1.6 | 3.6 | 2.9 | 2.5 |
| 18:1 | 2.8 | 4.9 | 16.7 | 3.8 | 8.3 | 38.0 | 4.9 | 12.9 | 46.9 | 3.5 | 6.1 | 68.8 |
| 18:2 | 12.6 | 11.5 | 6.8 | 13.3 | 13.8 | 4.9 | 20.7 | 18.3 | 5.2 | 28.0 | 30.4 | 4.4 |
| 18:3 | 50.6 | 50.3 | 46.0 | 54.2 | 50.0 | 33.5 | 40.4 | 33.2 | 25.3 | 43.8 | 38.7 | 12.3 |

EXAMPLE 12

Sequences of Mutant and Wild-Type Delta-12 Fatty Acid

Desaturases from *B. napus*

Primers specific for the FAD2 structural gene were used to clone the entire open reading frame (ORF) of the D and F 12-DES genes by reverse transcriptase polymerase chain reaction (RT-PCR). RNA from seeds of IMC129, Q508 and Westar plants was isolated by standard methods and was used as template. The RT-amplified fragments were used for nucleotide sequence determination. The DNA sequence of each gene from each line was determined from both strands by standard dideoxy sequencing methods.

Sequence analysis revealed a G to A transversion at nucleotide 316 (from the translation initiation codon) of the D gene in both IMC129 (SEQ ID NO:8) and Q508, compared to the sequence of Westar (SEQ ID NO:1). The transversion changes the codon at this position from GAG to AAG and results in a non-conservative substitution of glutamic acid, an acidic residue, for lysine a basic residue. The presence of the same mutation in both lines was expected since the Q508 line was derived from IMC129. The same base change was also detected in Q508 and IMC129 when RNA from leaf tissue was used as template.

The G to A mutation at nucleotide 316 was confirmed by sequencing several independent clones containing fragments amplified directly from genomic DNA of IMC129 and Westar. These results eliminated the possibility of a rare mutation introduced during reverse transcription and PCR in the RT-PCR protocol. It was concluded that the IMC129 mutant is due to a single base transversion at nucleotide 316 in the coding region of the D gene of rapeseed microsomal delta 12-desaturase.

A single base transition from T to A at nucleotide 515 of the F gene was detected in Q508 compared to the Westar sequence. The mutation changes the codon at this position from CTC to CAC, resulting in the non-conservative substitution of a non-polar residue, leucine, for a polar residue, histidine, in the resulting gene product. No mutations were found in the F gene sequence of IMC129 compared to the F gene sequence of Westar.

These data support the conclusion that a mutation in a delta-12 desaturase gene sequence results in alterations in the fatty acid profile of plants containing such a mutated gene. Moreover, the data show that when a plant line or species contains two delta-12 desaturase loci, the fatty acid profile of an individual having two mutated loci differs from the fatty acid profile of an individual having one mutated locus.

The mutation in the D gene of IMC129 and Q508 mapped to a region having a conserved amino acid motif (His-Xaa-Xaa-Xaa-His) found in cloned delta-12 and delta-15 membrane bound-desaturases (Table XX).

TABLE XX

Alignment of Amino Acid Sequences
of Cloned Canola Membrane Bound-Desaturases

| Desaturase Gene | Sequence[a] | Position[b] |
|---|---|---|
| Canola-fad2-D(129) | AHKCGH | 109 |
| Canola-FAd2-D | AHECGH | 109 |
| Canola-FAd2-F | AHECGH | 109 |
| Canola FadC | GHDCAH | 170 |
| Canola-Fad3 | GHDCGH | 96 |
| Canola-FadD | GHDCGH | 125 |

(FadD = Plastid delta 15, Fad3 = Microsomal delta-15),
(FadC = Plastid delta-12, Fad2 = Microsomal delta-12)
[a]One letter amino acid code; conservative substitutions are underlined; non-conservative substitutions are in bold.
[b]position of first amino acid in gene product.

EXAMPLE 13

Transcription and Translation of Microsomal Delta-12

Fatty Acid Desaturases

Transcription in vivo was analyzed by RT-PCR analysis of stage II and stage III developing seeds and leaf tissue. The primers used to specifically amplify 12-DES F gene RNA from the indicated tissues were sense primer 5'-GGATATGATGATGGTGAAAGA-3' and antisense primer 5'-TCTTTCACCATCATCATATCC-3'. The primers used to specifically amplify 12-DES D gene RNA from the indicated tissues were sense primer 5'-GTTATGAAGCAAAGAAGAAAC-3' and antisense primer 5'-GTTTCTTCTTTGCTTCATAAC-3'. The results indicated that mRNA of both the D and F gene was expressed in seed and leaf tissues of IMC129, Q508 and wild type Westar plants.

In vitro transcription and translation analysis showed that a peptide of about 46 kD was made. This is the expected size of both the D gene product and the F gene product, based on sum of the deduced amino acid sequence of each gene and the cotranslational addition of a microsomal membrane peptide.

These results rule out the possibility that nonsense or frameshift mutations, resulting in a truncated polypeptide gene product, are present in either the mutant D gene or the mutant F gene. The data, in conjunction with the data of Example 12, support the conclusion that the mutations in Q508 and IMC129 are in delta-12 fatty acid desaturase structural genes encoding desaturase enzymes, rather than in regulatory genes.

EXAMPLE 14

Development of Gene-Specific PCR Markers

Based on the single base change in the mutant D gene of IMC129 described in above, two 5' PCR printers were designed. The nucleotide sequence of the primers differed only in the base (G for Westar and A for IMC129) at the 3' end. The primers allow one to distinguish between mutant Can-Fad2-D-129 and wild-type Can-Fad2-D alleles in a DNA-based PCR assay. Since there is only a single base difference in the 5' PCR primers, the PCR assay is very sensitive to the PCR conditions such as annealing temperature, cycle number, amount, and purity of DNA templates used. Assay conditions have been established that distinguish between the mutant gene and the wild type gene using genomic DNA from IMC129 and wild type plants as templates. Conditions may be further optimized by varying PCR parameters, particularly with variable crude DNA samples. A PCR assay distinguishing the single base mutation in IMC129 from the wild type gene along with fatty acid composition analysis provides a means to simplify segregation and selection analysis of genetic crosses involving plants having a delta-12 fatty acid desaturase mutation.

To the extent not already indicated, it will be understood by those of ordinary skill in the art that any one of the various specific embodiments herein described and illustrated may be further modified to incorporate features shown in other of the specific embodiments.

The foregoing detailed description has been provided for a better understanding of the invention only and no unnecessary limitation should be understood therefrom as some modifications will be apparent to those skilled in the art without deviating from the spirit and scope of the appended claims.

---

What is claimed is:

1. An isolated nucleic acid comprising a full-length *Brassicaceae delta*-15 fatty acid desaturase coding sequence having at least one mutation in a region of said desaturase coding sequence encoding a His-Xaa-Xaa-Xaa-His amino acid motif, wherein said at least one mutation renders the product of said desaturase coding sequence non-functional and wherein said sequence includes said at least one mutation.

2. The nucleic acid fragment of claim 1, wherein said sequence encodes a microsomal gene product.

3. The nucleic acid fragment of claim 1, wherein said at least one mutation introduces a non-conservative amino acid substitution in said region.

4. The nucleic acid fragment of claim 3, wherein the wild-type amino acid sequence of said motif comprises the sequence His-Asp-Cys-Gly-His (SEQ ID NO:9).

5. The nucleic acid fragment of claim 4, wherein said

6. The nucleic acid fragment of claim 1, wherein said mutant desaturase coding sequence is from a *Brassica napus* plant.

7. A *Brassicacea* plant containing a full-length coding sequence of a delta-15 fatty acid desaturase gene having at least one mutation, wherein said at least one mutation is in a region encoding a His-Xaa-Xaa-Xaa-His amino acid motif and wherein said mutation renders the product of said desaturase gene non-functional.

8. The plant of claim 7, wherein said mutation confers a decreased level of α-linolenic acid in seeds of said plant.

9. The plant of claim 7, wherein said mutant desaturase gene encodes a microsomal gene product.

10. The plant of claim 7, wherein said at least one mutation comprises a non-conservative amino acid substitution in said region.

11. The plant of claim 10, wherein the wild-type amino acid sequence of said motif comprises the sequence His-Asp-Cys-Gly-His (SEQ ID NQ:9).

12. The plant of claim 11, wherein said at least one mutation comprises a codon encoding Lys in place of the codon encoding Asp.

13. The plant of claim 7, wherein said mutant desaturase gene is from a *Brassica napus* plant.

14. The plant of claim 7, wherein said plant is a *Brassica napus* plant.

15. A *Brassicacea* plant containing:
a) a full-length coding sequence from a delta-12 fatty acid desaturane gene having at least one mutation, said at least one delta-12 gene mutation in a region encoding a His-Xaa-Xaa-Xaa-His amino acid motif; and
b) a full-length coding sequence from a delta-15 fatty acid desaturase gene having at least one mutation, said at least one delta-15 gene mutation in a region encoding a His-Xaa-Xaa-Xaa-His amino acid motif,
wherein said delta-12 gene mutation and said delta-15 gene mutation render the products of said delta-12 desaturase gene and said delia-15 desaturase gene, respectively, non-functional.

16. The plant of claim 15, wherein said mutant genes confer a decreased level of α-linolenic acid in seeds of said plant compared to α-linolenic acid levels in corresponding seeds lacking said mutant genes.

17. A *Brassicaceae* or *Helianthus* plant containing a full-length coding sequence of a delta-12 fatty acid desaturase gene having at least one mutation, said at least one mutation in a region encoding a Tyr-Leu-Asn-Asn-Pro (SEQ ID NO:50) amino acid motif and wherein said mutation renders the product of said desaturase gene non-functional.

18. A method for producing a Brossicaceat or Helionihus plant line, comprising the steps of:
a) inducing mutagenesis in cells of a starting variety of a *Brassicaceae* or *Helianthus* species;
b) obtaining one or more plants from said cells;
c) identifying at least one of said plants that contains a delta-12 fatty acid desaturase gene having at least one mutation, said at least one mutation in a region encoding a His-Xaa-Xaa-Xaa-His amino acid motif, wherein said mutation in said delta-12 gene renders the product of said delta-12 desaturase gene non-functional; and
d) producing said *Brassicaceae* or *Helianthus* plant line from said at least one plant, said *Brassicaceae* or *Helianthus* plant line having said at least one mutation in said delta-12 gene.

19. The method of claim 18, wherein said plant line yields an oil having a stabilized linoleic acid content from about 2.0% to about 12.0%.

20. The method of claim 18, further comprising the steps of:
e) inducing mutagenesis in cells of said *Brassicaceae* or *Helianthus* plant line;
f) obtaining one or more plants from said cells of said *Brassicaceae* or *Helianthus* plant line;
g) identifying at least one of said plants from step f) that contains a delta-15 fatty acid desaturase gene having at least one mutation, wherein said at least one mutation in said delta-15 gene is in a region encoding a His-Xaa-Xaa-Xaa-His amino acid motif, wherein said mutation renders the product of said delta-15 desaturase gene non-functional; and
h) producing a second *Brassicaceae* or *Helianthus* plant line from said at least one plant identified in step g), said second plant line having said at least one mutation in said delta-12 gene and said at least one mutation in said delta-15 gene.

21. The method of claim 18, wherein said starting variety is a *Brassica napus* variety.

22. The method of claim 21, wherein said mutation is in a first form of delta-12 fatty acid desaturase.

23. The method of claim 22, further comprising the step of crossing a plant of said plant line to a plant having a mutation in a second form of delta-12 fatty acid desaturase.

24. The method of claim 23, wherein said second mutation is in a region other than a region encoding a His-Xaa-Xaa-Xaa-His amino acid motif.

25. The method of claim 22, further comprising the steps of:
e) inducing mutagenesis in cells of said *Brassicaceae* or *Helianthus* plant line;
f) obtaining one or more plants from said cells of said *Brassicaceae* or *Helianthus* plant line;
g) identifying at least one of said plants from step f) that contains a second delta-12 fatty acid desaturase gene having at least one mutation, said second gene mutation in a region other than a region encoding a His-Xaa-Xaa-Xaa-LJis amino acid motif; and
h) producing a second *Brassicaceae* or *Helianthus* plant line from said at least one plant identified in step g), said second *Brassicaceae* or *Helianthus* plant line having said first and second delta-12 gene mutations.

26. The method of claim 18, wherein said identifying step comprises a technique selected from the group consisting of: PCR, 3SR and direct polynucleotide sequencing.

27. A method for producing a *Brassicaceae* plant line, comprising the steps of:
  a) inducing mutagenesis in cells of a starting variety of a *Brassicaceac* species;
  b) obtaining one or more plants from said cells;
  c) identifying at least one of said plants that contains a delta-15 fatty acid desaturase gene having at least one mutation, said at least one mutation in a region encoding a His-Xaa-Xaa-Xaa-His amino acid motif, wherein said at least one mutation renders the product of said delta-15 desaturase gene non-functional; and
  d) producing said *Brassicaceae* plant line from said at least one plant, said *Brassicaceae* plant line having said mutation in said delta-15 gene.

28. The method of claim 27, wherein said identifying step comprises a technique selected from the group consisting of: PCR, 3SR and direct polynucleotide sequencing.

29. An isolated nucleic acid comprising a full length *Brassicaceae* or *Helianthus* delta-12 fatty acid desaturase coding sequence having at least one mutation in a region of said desaturase coding sequence encoding a Tyr-Leu-Asn-Asn-Pro (SEQ ID NO:50) amino acid motif, wherein said at least one mutation renders the product of said desaturase coding sequence non-functional and wherein said sequence includes said at least one mutation.

30. A method for identifying a mutation in a *Brassicaceae* plant, comprising:
  a) providing a *Brassicaceae* plant having a decreased α-linolenic acid content as compared with a corresponding control *Brassicaceae* plant; and
  b) identifying at least one mutation inn delta-15 fatty acid desaturase gene of said plant, said at least one mutation in a region encoding a His-Xaa-Xaa-Xaa-His amino acid motif, wherein said mutation renders the product of said delta-15 fatty acid desaturase gene non-functional.

31. The method of claim 30, wherein said identifying step comprises a technique selected from the group consisting of: PCR, 3SR and direct polynucleotide sequencing.

32. A method for identifying a mutation in a *Brassicaceae* or *Helianthus* plant, comprising:
  a) providing a *Brassicaceae* or *Helianthus* plant having an increased oleic acid content as compared with a corresponding control *Brassicaceae* or *Helianthus* plant; and
  b) identifying at least one mutation in a delta-12 fatty acid desaturase gene of said plant, said at least one mutation in a region encoding a His-Xaa-Xaa-Xaa-His amino acid motif, wherein said mutation renders the product of said delta-12 fatty acid desaturase gene non-functional.

33. The method of claim 32, wherein said identifying step comprises a technique selected from the group consisting of: PCR., 3SR and direct polynucleotide sequencing.

34. The nucleic acid fragment of claim 29, wherein said at least one mutation comprises a codon encoding His in place of the codon encoding Leu.

* * * * *

UNITED STATES PATENT AND TRADEMARK OFFICE
CERTIFICATE OF CORRECTION

PATENT NO. : 7,135,614 B1  Page 1 of 2
APPLICATION NO. : 08/572027
DATED : November 14, 2006
INVENTOR(S) : Lorin R. DeBonte, Zhegong Fan and Guo-Hua Miao It is certified that error appears in the above-identified patent and that said Letters Patent is hereby corrected as shown below:

Title Page, Item 56 Related U.S. Application Data, please delete entire paragraph;

Title Page, Item 56 References Cited, Other Publications, Williams et al. reference, please delete "J. Am. Assoc." and insert --J. Am. Med. Assoc.--therefor;

Column 55, line 4, please delete "desaturuse" and insert --desaturase--therefor;

Column 55, line 18, after "at" please insert --least one mutation comprises a codon encoding Lys in place of the codon encoding Asp.--;

Column 55, line 22, please delete "Brassicacea" and insert --Brassicaceae--therefor;

Column 55, line 45, please delete "Brassicacea" and insert --Brassicaceae--therefor;

Column 55, line 47, please delete "desaturane" and insert --desaturase--therefor;

Column 56, line 1, please delete "Brossicaceat" and insert --Brassicaceae--therefor;

Column 56, line 1, please delete "Helionihus" and insert --Helianthus--therefor;

Column 56, line 60, please delete "LJis" and insert --His--therefor;

Column 56, line 63, please delete "HeIianthus" and insert --Helianthus--therefor;

Column 57, line 4, please delete "Brassicaceac" and insert --Brassicaceae--therefor;

Column 57, lines 29-31, please delete "plant having a decreased $\alpha$-linolenic acid content as compared with a corresponding control" and insert --plant having a decreased $\alpha$-linolenic acid content as compared with a corresponding control--therefor;

Column 57, line 31, please delete "plant; and" and insert --plant; and--therefor;

UNITED STATES PATENT AND TRADEMARK OFFICE
CERTIFICATE OF CORRECTION

| | | |
|---|---|---|
| PATENT NO. | : 7,135,614 B1 | Page 2 of 2 |
| APPLICATION NO. | : 08/572027 | |
| DATED | : November 14, 2006 | |
| INVENTOR(S) | : Lorin R. DeBonte, Zhegong Fan and Guo-Hua Miao | |

It is certified that error appears in the above-identified patent and that said Letters Patent is hereby corrected as shown below:

Column 58, line 1, please delete "inn" and insert --in a--therefor.

Signed and Sealed this

Tenth Day of July, 2007

JON W. DUDAS
*Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1155 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
      (A) ORGANISM: Brassica napus (ix) FEATURE:
      (D) OTHER INFORMATION: Wild type F form.

(xi) SEQUENCE DESCRIPTION: SEQ ID NO:1:

```
ATG GGT GCA GGT GGA AGA ATG CAA GTG TCT CCT CCC TCC AAG AAG TCT       48
Met Gly Ala Gly Gly Arg Met Gln Val Ser Pro Pro Ser Lys Lys Ser
 1               5                  10                  15

GAA ACC GAC ACC ATC AAG CGC GTA CCC TGC GAG ACA CCG CCC TTC ACT       96
Glu Thr Asp Thr Ile Lys Arg Val Pro Cys Glu Thr Pro Pro Phe Thr
                20                  25                  30

GTC GGA GAA CTC AAG AAA GCA ATC CCA CCG CAC TGT TTC AAA CGC TCG      144
Val Gly Glu Leu Lys Lys Ala Ile Pro Pro His Cys Phe Lys Arg Ser
            35                  40                  45

ATC CCT CGC TCT TTC TCC TAC CTC ATC TGG GAC ATC ATC ATA GCC TCC      192
Ile Pro Arg Ser Phe Ser Tyr Leu Ile Trp Asp Ile Ile Ile Ala Ser
        50                  55                  60

TGC TTC TAC TAC NTC GCC ACC ACT TAC TTC CCT CTC CTC CCT CAC CCT      240
Cys Phe Tyr Tyr Xaa Ala Thr Thr Tyr Phe Pro Leu Leu Pro His Pro
    65                  70                  75                  80

CTC TCC TAC TTC GCC TGG CCT CTC TAC TGG GCC TGC CAA GGG TGC GTC      288
Leu Ser Tyr Phe Ala Trp Pro Leu Tyr Trp Ala Cys Gln Gly Cys Val
```

-continued

```
                          85                   90                   95
CTA ACC GGC GTC TGG GTC ATA GCC CAC GAA TGC GGC CAC CAC GCC TTC          336
Leu Thr Gly Val Trp Val Ile Ala His Glu Cys Gly His His Ala Phe
            100                 105                 110

AGC GAC TAC CAG TGG CTT GAC GAC ACC GTC GGT CTC ATC TTC CAC TCC          384
Ser Asp Tyr Gln Trp Leu Asp Asp Thr Val Gly Leu Ile Phe His Ser
            115                 120                 125

TTC CTC CTC GTC CCT TAC TTC TCC TGG AAG TAC AGT CAT CGC AGC CAC          432
Phe Leu Leu Val Pro Tyr Phe Ser Trp Lys Tyr Ser His Arg Ser His
        130                 135                 140

CAT TCC AAC ACT GGC TCC CTC GAG AGA GAC GAA GTG TTT GTC CCC AAG          480
His Ser Asn Thr Gly Ser Leu Glu Arg Asp Glu Val Phe Val Pro Lys
145                 150                 155                 160

AAG AAG TCA GAC ATC AAG TGG TAC GGC AAG TAC CTC AAC AAC CCT TTG          528
Lys Lys Ser Asp Ile Lys Trp Tyr Gly Lys Tyr Leu Asn Asn Pro Leu
                165                 170                 175

GGA CGC ACC GTG ATG TTA ACG GTT CAG TTC ACT CTC GGC TGG CCG TTG          576
Gly Arg Thr Val Met Leu Thr Val Gln Phe Thr Leu Gly Trp Pro Leu
            180                 185                 190

TAC TTA GCC TTC AAC GTC TCG GGA AGA CCT TAC GAC GGC GGC TTC CGT          624
Tyr Leu Ala Phe Asn Val Ser Gly Arg Pro Tyr Asp Gly Gly Phe Arg
            195                 200                 205

TGC CAT TTC CAC CCC AAC GCT CCC ATC TAC AAC GAC CGC GAG CGT CTC          672
Cys His Phe His Pro Asn Ala Pro Ile Tyr Asn Asp Arg Glu Arg Leu
        210                 215                 220

CAG ATA TAC ATC TCC GAC GCT GGC ATC CTC GCC GTC TGC TAC GGT CTC          720
Gln Ile Tyr Ile Ser Asp Ala Gly Ile Leu Ala Val Cys Tyr Gly Leu
225                 230                 235                 240

TTC CGT TAC GCC GCC GGC CAG GGA GTG GCC TCG ATG GTC TGC TTC TAC          768
Phe Arg Tyr Ala Ala Gly Gln Gly Val Ala Ser Met Val Cys Phe Tyr
                245                 250                 255

GGA GTC CCG CTT CTG ATT GTC AAT GGT TTC CTC GTG TTG ATC ACT TAC          816
Gly Val Pro Leu Leu Ile Val Asn Gly Phe Leu Val Leu Ile Thr Tyr
            260                 265                 270

TTG CAG CAC ACG CAT CCT TCC CTG CCT CAC TAC GAT TCG TCC GAG TGG          864
Leu Gln His Thr His Pro Ser Leu Pro His Tyr Asp Ser Ser Glu Trp
            275                 280                 285

GAT TGG TTC AGG GGA GCT TTG GCT ACC GTT GAC AGA GAC TAC GGA ATC          912
Asp Trp Phe Arg Gly Ala Leu Ala Thr Val Asp Arg Asp Tyr Gly Ile
        290                 295                 300

TTG AAC AAG GTC TTC CAC AAT ATT ACC GAC ACG CAC GTG GCC CAT CAT          960
Leu Asn Lys Val Phe His Asn Ile Thr Asp Thr His Val Ala His His
305                 310                 315                 320

CCG TTC TCC ACG ATG CCG CAT TAT CAC GCG ATG GAA GCT ACC AAG GCG         1008
Pro Phe Ser Thr Met Pro His Tyr His Ala Met Glu Ala Thr Lys Ala
                325                 330                 335

ATA AAG CCG ATA CTG GGA GAG TAT TAT CAG TTC GAT GGG ACG CCG GTG         1056
Ile Lys Pro Ile Leu Gly Glu Tyr Tyr Gln Phe Asp Gly Thr Pro Val
            340                 345                 350

GTT AAG GCG ATG TGG AGG GAG GCG AAG GAG TGT ATC TAT GTG GAA CCG         1104
Val Lys Ala Met Trp Arg Glu Ala Lys Glu Cys Ile Tyr Val Glu Pro
            355                 360                 365

GAC AGG CAA GGT GAG AAG AAA GGT GTG TTC TGG TAC AAC AAT AAG TTA T       1153
Asp Arg Gln Gly Glu Lys Lys Gly Val Phe Trp Tyr Asn Asn Lys Leu
        370                 375                 380

GA                                                                      1155
```

(2) INFORMATION FOR SEQ ID NO:2:

(i) SEQUENCE CHARACTERISTICS:
    (A) LENGTH: 384 amino acids
    (B) TYPE: amino acid
    (D) TOPOLOGY: linear (ii) MOLECULE TYPE: protein (xi) SEQUENCE DESCRIPTION: SEQ ID NO:2:

```
Met Gly Ala Gly Gly Arg Met Gln Val Ser Pro Pro Ser Lys Lys Ser
  1               5                  10                  15

Glu Thr Asp Thr Ile Lys Arg Val Pro Cys Glu Thr Pro Pro Phe Thr
             20                  25                  30

Val Gly Glu Leu Lys Lys Ala Ile Pro Pro His Cys Phe Lys Arg Ser
         35                  40                  45

Ile Pro Arg Ser Phe Ser Tyr Leu Ile Trp Asp Ile Ile Ala Ser
     50                  55                  60

Cys Phe Tyr Tyr Xaa Ala Thr Thr Tyr Phe Pro Leu Leu Pro His Pro
 65              70                  75                  80

Leu Ser Tyr Phe Ala Trp Pro Leu Tyr Trp Ala Cys Gln Gly Cys Val
                 85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Ser His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
                180                 185                 190

Tyr Leu Ala Phe Asn Val Ser Gly Arg Pro Tyr Asp Gly Gly Phe Arg
            195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Phe Arg Tyr Ala Ala Gly Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
            275                 280                 285

Asp Trp Phe Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Pro Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
```

-continued

```
      370             375             380
```

(2) INFORMATION FOR SEQ ID NO:3:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Brassica napus (vii) IMMEDIATE SOURCE:
        (B) CLONE: Q508

(ix) FEATURE:
        (D) OTHER INFORMATION: T to A transversion
            mutation at nucleotide 515 of the F form.

(xi) SEQUENCE DESCRIPTION: SEQ ID NO:3:

```
ATG GGT GCA GGT GGA AGA ATG CAA GTG TCT CCT CCC TCC AAG AAG TCT        48
Met Gly Ala Gly Gly Arg Met Gln Val Ser Pro Pro Ser Lys Lys Ser
 1               5                  10                  15

GAA ACC GAC ACC ATC AAG CGC GTA CCC TGC GAG ACA CCG CCC TTC ACT        96
Glu Thr Asp Thr Ile Lys Arg Val Pro Cys Glu Thr Pro Pro Phe Thr
             20                  25                  30

GTC GGA GAA CTC AAG AAA GCA ATC CCA CCG CAC TGT TTC AAA CGC TCG       144
Val Gly Glu Leu Lys Lys Ala Ile Pro Pro His Cys Phe Lys Arg Ser
         35                  40                  45

ATC CCT CGC TCT TTC TCC TAC CTC ATC TGG GAC ATC ATA GCC TCC           192
Ile Pro Arg Ser Phe Ser Tyr Leu Ile Trp Asp Ile Ile Ala Ser
     50                  55                  60

TGC TTC TAC TAC NTC GCC ACC ACT TAC TTC CCT CTC CTC CCT CAC CCT       240
Cys Phe Tyr Tyr Xaa Ala Thr Thr Tyr Phe Pro Leu Leu Pro His Pro
 65                  70                  75                  80

CTC TCC TAC TTC GCC TGG CCT CTC TAC TGG GCC TGC CAA GGG TGC GTC       288
Leu Ser Tyr Phe Ala Trp Pro Leu Tyr Trp Ala Cys Gln Gly Cys Val
                 85                  90                  95

CTA ACC GGC GTC TGG GTC ATA GCC CAC GAG TGC GGC CAC CAC GCC TTC       336
Leu Thr Gly Val Trp Val Ile Ala His Glu Cys Gly His His Ala Phe
            100                 105                 110

AGC GAC TAC CAG TGG CTT GAC GAC ACC GTC GGT CTC ATC TTC CAC TCC       384
Ser Asp Tyr Gln Trp Leu Asp Asp Thr Val Gly Leu Ile Phe His Ser
            115                 120                 125

TTC CTC CTC GTC CCT TAC TTC TCC TGG AAG TAC AGT CAT CGC AGC CAC       432
Phe Leu Leu Val Pro Tyr Phe Ser Trp Lys Tyr Ser His Arg Ser His
        130                 135                 140

CAT TCC AAC ACT GGC TCC CTC GAG AGA GAC GAA GTG TTT GTC CCC AAG       480
His Ser Asn Thr Gly Ser Leu Glu Arg Asp Glu Val Phe Val Pro Lys
145                 150                 155                 160

AAG AAG TCA GAC ATC AAG TGG TAC GGC AAG TAC CAC AAC AAC CCT TTG       528
Lys Lys Ser Asp Ile Lys Trp Tyr Gly Lys Tyr His Asn Asn Pro Leu
                165                 170                 175

GGA CGC ACC GTG ATG TTA ACG GTT CAG TTC ACT CTC GGC TGG CCG TTG       576
Gly Arg Thr Val Met Leu Thr Val Gln Phe Thr Leu Gly Trp Pro Leu
            180                 185                 190

TAC TTA GCC TTC AAC GTC TCG GGA AGA CCT TAC GAC GGC GGC TTC CGT       624
Tyr Leu Ala Phe Asn Val Ser Gly Arg Pro Tyr Asp Gly Gly Phe Arg
```

```
                195                 200                 205
TGC CAT TTC CAC CCC AAC GCT CCC ATC TAC AAC GAC CGC GAG CGT CTC        672
Cys His Phe His Pro Asn Ala Pro Ile Tyr Asn Asp Arg Glu Arg Leu
        210                 215                 220

CAG ATA TAC ATC TCC GAC GCT GGC ATC CTC GCC GTC TGC TAC GGT CTC        720
Gln Ile Tyr Ile Ser Asp Ala Gly Ile Leu Ala Val Cys Tyr Gly Leu
225                 230                 235                 240

TTC CGT TAC GCC GCC GGC CAG GGA GTG GCC TCG ATG GTC TGC TTC TAC        768
Phe Arg Tyr Ala Ala Gly Gln Gly Val Ala Ser Met Val Cys Phe Tyr
                245                 250                 255

GGA GTC CCG CTT CTG ATT GTC AAT GGT TTC CTC GTG TTG ATC ACT TAC        816
Gly Val Pro Leu Leu Ile Val Asn Gly Phe Leu Val Leu Ile Thr Tyr
        260                 265                 270

TTG CAG CAC ACG CAT CCT TCC CTG CCT CAC TAC GAT TCG TCC GAG TGG        864
Leu Gln His Thr His Pro Ser Leu Pro His Tyr Asp Ser Ser Glu Trp
            275                 280                 285

GAT TGG TTC AGG GGA GCT TTG GCT ACC GTT GAC AGA GAC TAC GGA ATC        912
Asp Trp Phe Arg Gly Ala Leu Ala Thr Val Asp Arg Asp Tyr Gly Ile
290                 295                 300

TTG AAC AAG GTC TTC CAC AAT ATT ACC GAC ACG CAC GTG GCC CAT CAT        960
Leu Asn Lys Val Phe His Asn Ile Thr Asp Thr His Val Ala His His
305                 310                 315                 320

CCG TTC TCC ACG ATG CCG CAT TAT CAC GCG ATG GAA GCT ACC AAG GCG       1008
Pro Phe Ser Thr Met Pro His Tyr His Ala Met Glu Ala Thr Lys Ala
                325                 330                 335

ATA AAG CCG ATA CTG GGA GAG TAT TAT CAG TTC GAT GGG ACG CCG GTG       1056
Ile Lys Pro Ile Leu Gly Glu Tyr Tyr Gln Phe Asp Gly Thr Pro Val
                340                 345                 350

GTT AAG GCG ATG TGG AGG GAG GCG AAG GAG TGT ATC TAT GTG GAA CCG       1104
Val Lys Ala Met Trp Arg Glu Ala Lys Glu Cys Ile Tyr Val Glu Pro
        355                 360                 365

GAC AGG CAA GGT GAG AAG AAA GGT GTG TTC TGG TAC AAC AAT AAG TTA T     1153
Asp Arg Gln Gly Glu Lys Lys Gly Val Phe Trp Tyr Asn Asn Lys Leu
370                 375                 380

GA                                                                    1155

(2) INFORMATION FOR SEQ ID NO:4:

(i) SEQUENCE CHARACTERISTICS:
        (A) LENGTH: 384 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ile Ala Ser
        50                  55                  60

Cys Phe Tyr Tyr Xaa Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
```

-continued

```
                    100                 105                 110
Ser Asp Tyr Gln Trp Leu Asp Thr Val Gly Leu Ile Phe His Ser
        115                 120                 125

Phe Leu Leu Val Pro Tyr Phe Ser Trp Lys Tyr Ser His Arg Ser His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr His Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Arg
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Phe Arg Tyr Ala Ala Gly Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Phe Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Pro Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly val Phe Trp Tyr Asn Asn Lys Leu
    370                 375                 380
```

(2) INFORMATION FOR SEQ ID NO:5:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Brassica napus (ix) FEATURE:
        (D) OTHER INFORMATION: Wild type D form.

(xi) SEQUENCE DESCRIPTION: SEQ ID NO:5:

```
ATG GGT GCA GGT GGA AGA ATG CAA GTG TCT CCT CCC TCC AAA AAG TCT    48
Met Gly Ala Gly Gly Arg Met Gln Val Ser Pro Pro Ser Lys Lys Ser
1               5                   10                  15
```

-continued

| | |
|---|---|
| GAA ACC GAC AAC ATC AAG CGC GTA CCC TGC GAG ACA CCG CCC TTC ACT<br>Glu Thr Asp Asn Ile Lys Arg Val Pro Cys Glu Thr Pro Pro Phe Thr<br>            20                    25                    30 | 96 |
| GTC GGA GAA CTC AAG AAA GCA ATC CCA CCG CAC TGT TTC AAA CGC TCG<br>Val Gly Glu Leu Lys Lys Ala Ile Pro Pro His Cys Phe Lys Arg Ser<br>       35                    40                    45 | 144 |
| ATC CCT CGC TCT TTC TCC TAC CTC ATC TGG GAC ATC ATC ATA GCC TCC<br>Ile Pro Arg Ser Phe Ser Tyr Leu Ile Trp Asp Ile Ile Ile Ala Ser<br>50                    55                    60 | 192 |
| TGC TTC TAC TAC GTC GCC ACC ACT TAC TTC CCT CTC CTC CCT CAC CCT<br>Cys Phe Tyr Tyr Val Ala Thr Thr Tyr Phe Pro Leu Leu Pro His Pro<br>65                    70                    75                    80 | 240 |
| CTC TCC TAC TTC GCC TGG CCT CTC TAC TGG GCC TGC CAG GGC TGC GTC<br>Leu Ser Tyr Phe Ala Trp Pro Leu Tyr Trp Ala Cys Gln Gly Cys Val<br>                 85                    90                    95 | 288 |
| CTA ACC GGC GTC TGG GTC ATA GCC CAC GAG TGC GGC CAC CAC GCC TTC<br>Leu Thr Gly Val Trp Val Ile Ala His Glu Cys Gly His His Ala Phe<br>            100                   105                 110 | 336 |
| AGC GAC TAC CAG TGG CTG GAC GAC ACC GTC GGC CTC ATC TTC CAC TCC<br>Ser Asp Tyr Gln Trp Leu Asp Asp Thr Val Gly Leu Ile Phe His Ser<br>            115                   120                 125 | 384 |
| TTC CTC CTC GTC CCT TAC TTC TCC TGG AAG TAC AGT CAT CGA CGC CAC<br>Phe Leu Leu Val Pro Tyr Phe Ser Trp Lys Tyr Ser His Arg Arg His<br>130                    135                 140 | 432 |
| CAT TCC AAC ACT GGC TCC CTC GAG AGA GAC GAA GTG TTT GTC CCC AAG<br>His Ser Asn Thr Gly Ser Leu Glu Arg Asp Glu Val Phe Val Pro Lys<br>145                    150                 155                 160 | 480 |
| AAG AAG TCA GAC ATC AAG TGG TAC GGC AAG TAC CTC AAC AAC CCT TTG<br>Lys Lys Ser Asp Ile Lys Trp Tyr Gly Lys Tyr Leu Asn Asn Pro Leu<br>            165                   170                 175 | 528 |
| GGA CGC ACC GTG ATG TTA ACG GTT CAG TTC ACT CTC GGC TGG CCT TTG<br>Gly Arg Thr Val Met Leu Thr Val Gln Phe Thr Leu Gly Trp Pro Leu<br>            180                   185                 190 | 576 |
| TAC TTA GCC TTC AAC GTC TCG GGG AGA CCT TAC GAC GGC GGC TTC GCT<br>Tyr Leu Ala Phe Asn Val Ser Gly Arg Pro Tyr Asp Gly Gly Phe Ala<br>            195                   200                 205 | 624 |
| TGC CAT TTC CAC CCC AAC GCT CCC ATC TAC AAC GAC CGC GAG CGT CTC<br>Cys His Phe His Pro Asn Ala Pro Ile Tyr Asn Asp Arg Glu Arg Leu<br>210                    215                 220 | 672 |
| CAG ATA TAC ATC TCC GAC GCT GGC ATC CTC GCC GTC TGC TAC GGT CTC<br>Gln Ile Tyr Ile Ser Asp Ala Gly Ile Leu Ala Val Cys Tyr Gly Leu<br>225                    230                 235                 240 | 720 |
| TAC CGC TAC GCT GCT GTC CAA GGA GTT GCC TCG ATG GTC TGC TTC TAC<br>Tyr Arg Tyr Ala Ala Val Gln Gly Val Ala Ser Met Val Cys Phe Tyr<br>            245                   250                 255 | 768 |
| GGA GTT CCG CTT CTG ATT GTC AAT GGG TTC TTA GTT TTG ATC ACT TAC<br>Gly Val Pro Leu Leu Ile Val Asn Gly Phe Leu Val Leu Ile Thr Tyr<br>            260                   265                 270 | 816 |
| TTG CAG CAC ACG CAT CCT TCC CTG CCT CAC TAT GAC TCG TCT GAG TGG<br>Leu Gln His Thr His Pro Ser Leu Pro His Tyr Asp Ser Ser Glu Trp<br>            275                   280                 285 | 864 |
| GAT TGG TTG AGG GGA GCT TTG GCC ACC GTT GAC AGA GAC TAC GGA ATC<br>Asp Trp Leu Arg Gly Ala Leu Ala Thr Val Asp Arg Asp Tyr Gly Ile<br>            290                   295                 300 | 912 |
| TTG AAC AAG GTC TTC CAC AAT ATC ACG GAC ACG CAC GTG GCG CAT CAC<br>Leu Asn Lys Val Phe His Asn Ile Thr Asp Thr His Val Ala His His<br>305                    310                 315                 320 | 960 |
| CTG TTC TCG ACC ATG CCG CAT TAT CAT GCG ATG GAA GCT ACG AAG GCG<br>Leu Phe Ser Thr Met Pro His Tyr His Ala Met Glu Ala Thr Lys Ala | 1008 |

```
                    325                 330                 335
ATA AAG CCG ATA CTG GGA GAG TAT TAT CAG TTG CAT GGG ACG CCG GTG     1056
Ile Lys Pro Ile Leu Gly Glu Tyr Tyr Gln Leu His Gly Thr Pro Val
            340                 345                 350

GTT AAG GCG ATG TGG AGG GAG GCG AAG GAG TGT ATC TAT GTG GAA CCG     1104
Val Lys Ala Met Trp Arg Glu Ala Lys Glu Cys Ile Tyr Val Glu Pro
        355                 360                 365

GAC AGG CAA GGT GAG AAA GGT GTG TTC TGG TAC AAC AAT AAG TTA T       1153
Asp Arg Gln Gly Glu Lys Lys Gly Val Phe Trp Tyr Asn Asn Lys Leu
    370                 375                 380

GA                                                                   1155

(2) INFORMATION FOR SEQ ID NO:6:

(i) SEQUENCE CHARACTERISTICS:
        (A) LENGTH: 384 amino acids
        (B) TYPE: amino acid
        (D) TOPOLOGY: linear (ii) MOLECULE TYPE: protein (xi) SEQUENCE DESCRIPTION: SEQ ID NO:6:

Met Gly Ala Gly Gly Arg Met Gln Val Ser Pro Ser Lys Lys Ser
 1               5                  10                  15

Glu Thr Asp Asn Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Val Ala Thr Thr Tyr Phe Pro Leu Leu Pro His Pro
 65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270
```

```
Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
        290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Leu His Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
370                 375                 380
```

(2) INFORMATION FOR SEQ ID NO:7:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM: Brassica napus (vii) IMMEDIATE SOURCE:
        (B) CLONE: IMC129

(ix) FEATURE:
        (D) OTHER INFORMATION: G to A transversion
            mutation at nucleotide 316 of the D form.

(xi) SEQUENCE DESCRIPTION: SEQ ID NO:7:

```
ATG GGT GCA GGT GGA AGA ATG CAA GTG TCT CCT CCC TCC AAA AAG TCT      48
Met Gly Ala Gly Gly Arg Met Gln Val Ser Pro Pro Ser Lys Lys Ser
1               5                   10                  15

GAA ACC GAC AAC ATC AAG CGC GTA CCC TGC GAG ACA CCG CCC TTC ACT      96
Glu Thr Asp Asn Ile Lys Arg Val Pro Cys Glu Thr Pro Pro Phe Thr
                20                  25                  30

GTC GGA GAA CTC AAG AAA GCA ATC CCA CCG CAC TGT TTC AAA CGC TCG     144
Val Gly Glu Leu Lys Lys Ala Ile Pro Pro His Cys Phe Lys Arg Ser
            35                  40                  45

ATC CCT CGC TCT TTC TCC TAC CTC ATC TGG GAC ATC ATA ATA GCC TCC     192
Ile Pro Arg Ser Phe Ser Tyr Leu Ile Trp Asp Ile Ile Ile Ala Ser
        50                  55                  60

TGC TTC TAC TAC GTC GCC ACC ACT TAC TTC CCT CTC CTC CCT CAC CCT     240
Cys Phe Tyr Tyr Val Ala Thr Thr Tyr Phe Pro Leu Leu Pro His Pro
65                  70                  75                  80

CTC TCC TAC TTC GCC TGG CCT CTC TAC TGG GCC TGC CAG GGC TGC GTC     288
Leu Ser Tyr Phe Ala Trp Pro Leu Tyr Trp Ala Cys Gln Gly Cys Val
                85                  90                  95

CTA ACC GGC GTC TGG GTC ATA GCC CAC AAG TGC GGC CAC CAC GCC TTC     336
Leu Thr Gly Val Trp Val Ile Ala His Lys Cys Gly His His Ala Phe
                100                 105                 110

AGC GAC TAC CAG TGG CTG GAC GAC ACC GTC GGC CTC ATC TTC CAC TCC     384
Ser Asp Tyr Gln Trp Leu Asp Asp Thr Val Gly Leu Ile Phe His Ser
                115                 120                 125
```

```
TTC CTC CTC GTC CCT TAC TTC TCC TGG AAG TAC AGT CAT CGA CGC CAC      432
Phe Leu Leu Val Pro Tyr Phe Ser Trp Lys Tyr Ser His Arg Arg His
    130                 135                 140

CAT TCC AAC ACT GGC TCC CTC GAG AGA GAC GAA GTG TTT GTC CCC AAG      480
His Ser Asn Thr Gly Ser Leu Glu Arg Asp Glu Val Phe Val Pro Lys
145                 150                 155                 160

AAG AAG TCA GAC ATC AAG TGG TAC GGC AAG TAC CTC AAC AAC CCT TTG      528
Lys Lys Ser Asp Ile Lys Trp Tyr Gly Lys Tyr Leu Asn Asn Pro Leu
                165                 170                 175

GGA CGC ACC GTG ATG TTA ACG GTT CAG TTC ACT CTC GGC TGG CCT TTG      576
Gly Arg Thr Val Met Leu Thr Val Gln Phe Thr Leu Gly Trp Pro Leu
            180                 185                 190

TAC TTA GCC TTC AAC GTC TCG GGG AGA CCT TAC GAC GGC GGC TTC GCT      624
Tyr Leu Ala Phe Asn Val Ser Gly Arg Pro Tyr Asp Gly Gly Phe Ala
        195                 200                 205

TGC CAT TTC CAC CCC AAC GCT CCC ATC TAC AAC GAC CGC GAG CGT CTC      672
Cys His Phe His Pro Asn Ala Pro Ile Tyr Asn Asp Arg Glu Arg Leu
    210                 215                 220

CAG ATA TAC ATC TCC GAC GCT GGC ATC CTC GCC GTC TGC TAC GGT CTC      720
Gln Ile Tyr Ile Ser Asp Ala Gly Ile Leu Ala Val Cys Tyr Gly Leu
225                 230                 235                 240

TAC CGC TAC GCT GCT GTC CAA GGA GTT GCC TCG ATG GTC TGC TTC TAC      768
Tyr Arg Tyr Ala Ala Val Gln Gly Val Ala Ser Met Val Cys Phe Tyr
                245                 250                 255

GGA GTT CCG CTT CTG ATT GTC AAT GGG TTC TTA GTT TTG ATC ACT TAC      816
Gly Val Pro Leu Leu Ile Val Asn Gly Phe Leu Val Leu Ile Thr Tyr
            260                 265                 270

TTG CAG CAC ACG CAT CCT TCC CTG CCT CAC TAT GAC TCG TCT GAG TGG      864
Leu Gln His Thr His Pro Ser Leu Pro His Tyr Asp Ser Ser Glu Trp
        275                 280                 285

GAT TGG TTG AGG GGA GCT TTG GCC ACC GTT GAC AGA GAC TAC GGA ATC      912
Asp Trp Leu Arg Gly Ala Leu Ala Thr Val Asp Arg Asp Tyr Gly Ile
    290                 295                 300

TTG AAC AAG GTC TTC CAC AAT ATC ACG GAC ACG CAC GTG GCG CAT CAC      960
Leu Asn Lys Val Phe His Asn Ile Thr Asp Thr His Val Ala His His
305                 310                 315                 320

CTG TTC TCG ACC ATG CCG CAT TAT CAT GCG ATG GAA GCT ACG AAG GCG     1008
Leu Phe Ser Thr Met Pro His Tyr His Ala Met Glu Ala Thr Lys Ala
                325                 330                 335

ATA AAG CCG ATA CTG GGA GAG TAT TAT CAG TTG CAT GGG ACG CCG GTG     1056
Ile Lys Pro Ile Leu Gly Glu Tyr Tyr Gln Leu His Gly Thr Pro Val
            340                 345                 350

GTT AAG GCG ATG TGG AGG GAG GCG AAG GAG TGT ATC TAT GTG GAA CCG     1104
Val Lys Ala Met Trp Arg Glu Ala Lys Glu Cys Ile Tyr Val Glu Pro
        355                 360                 365

GAC AGG CAA GGT GAG AAG AAA GGT GTG TTC TGG TAC AAC AAT AAG TTA T   1153
Asp Arg Gln Gly Glu Lys Lys Gly Val Phe Trp Tyr Asn Asn Lys Leu
    370                 375                 380

GA                                                                   1155

(2) INFORMATION FOR SEQ ID NO:8:

(i) SEQUENCE CHARACTERISTICS:
        (A) LENGTH: 384 amino acids
        (B) TYPE: amino acid
        (D) TOPOLOGY: linear (ii) MOLECULE TYPE: protein (xi) SEQUENCE DESCRIPTION: SEQ ID NO:8:
```

-continued

```
Met Gly Ala Gly Gly Arg Met Gln Val Ser Pro Pro Ser Lys Lys Ser
 1               5                  10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Lys Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Leu His Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
370                 375                 380
```